(12) United States Patent
Johnson et al.

(10) Patent No.: US 12,042,302 B2
(45) Date of Patent: Jul. 23, 2024

(54) ENHANCED INGESTIBLE EVENT INDICATORS AND METHODS FOR MAKING AND USING THE SAME

(71) Applicant: OTSUKA PHARMACEUTICAL CO., LTD., Tokyo (JP)

(72) Inventors: Patricia Johnson, San Carlos, CA (US); Raymond Schmidt, San Mateo, CA (US); Anuj Patel, San Francisco, CA (US); Kevin Cheng, San Francisco, CA (US); Kosuke Iwai, Berkeley, CA (US); Hooman Hafezi, Redwood City, CA (US)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 488 days.

(21) Appl. No.: 17/326,435

(22) Filed: May 21, 2021

(65) Prior Publication Data

US 2021/0338166 A1    Nov. 4, 2021

Related U.S. Application Data

(63) Continuation of application No. 15/116,198, filed as application No. PCT/US2015/014180 on Feb. 3, 2015, now abandoned.

(60) Provisional application No. 61/935,768, filed on Feb. 4, 2014.

(51) Int. Cl.
| | | |
|---|---|---|
| A61B 5/00 | (2006.01) | |
| A61B 5/07 | (2006.01) | |
| A61B 5/1473 | (2006.01) | |
| A61K 9/00 | (2006.01) | |
| A61K 9/20 | (2006.01) | |

(52) U.S. Cl.
CPC ............ *A61B 5/6861* (2013.01); *A61B 5/073* (2013.01); *A61B 5/1473* (2013.01); *A61B 5/4839* (2013.01); *A61B 5/7282* (2013.01); *A61K 9/0097* (2013.01); *A61K 9/20* (2013.01); *A61B 2562/125* (2013.01)

(58) Field of Classification Search
CPC ..... A61B 5/6861; A61B 5/073; A61B 5/1473; A61B 5/4839; A61B 5/7282; A61B 2562/125; A61K 9/0097; A61K 9/20
See application file for complete search history.

(56) References Cited

U.S. PATENT DOCUMENTS

| | | | | |
|---|---|---|---|---|
| 2010/0069717 | A1* | 3/2010 | Hafezi | A61P 25/04 600/117 |
| 2011/0054265 | A1* | 3/2011 | Hafezi | A61B 5/14546 600/300 |
| 2012/0004520 | A1* | 1/2012 | Whitworth | H01Q 1/273 600/302 |

* cited by examiner

*Primary Examiner* — Andrey Shostak
(74) *Attorney, Agent, or Firm* — Pillsbury Winthrop Shaw Pittman LLP

(57) ABSTRACT

Improved ingestible event markers are provided. Aspects of the markers may include the presence of a matrix layer that includes a binder and source of an electron acceptor. Alternatively or in addition to the matrix layer, aspects of the markers may include a large surface area electrode having a surface area that exceeds the surface area of the circuitry of the marker. Aspects further include methods of making and using the ingestible event markers.

12 Claims, 21 Drawing Sheets

ENHANCED INGESTIBLE EVENT INDICATORS AND METHODS FOR MAKING AND USING THE SAME

CROSS-REFERENCE TO RELATED APPLICATIONS

This application claims priority to U.S. Provisional Application No. 61/935,768, filed Feb. 4, 2014, entitled ENHANCED INGESTIBLE EVENT INDICATORS AND METHODS FOR MAKING AND USING THE SAME, the disclosure of which is incorporated herein by reference in its entirety.

INTRODUCTION

A variety of different ingestible compositions have been developed for nutritional, therapeutic and non-therapeutic uses. Examples of different types of ingestible compositions include orally ingestible tablets, capsules and liquids. A given orally ingestible formulation may include a variety of different components, such as active agents, carrier materials (including binders, bulking agents and other excipients), flavoring agents, coloring agents, etc.

More recently, ingestible compositions which include a device component, such as an ingestible event marker, have been developed. Use of such ingestible devices allows one to monitor the actual ingestion of an ingestible composition, and has broad applicability to a variety of different applications.

Furthermore, ingestible devices that include electronic circuitry have been proposed for use in a variety of different medical applications, including both diagnostic and therapeutic applications. These devices typically require an internal power supply for operation, such as an internal and self-contained power source. The electronic circuit components of the device are enclosed by an inert indigestible housing (e.g., glass housing) that passes through the body internally. Other examples include an ingestible data recorder capsule medical device that includes electronic circuits (e.g., sensor, recorder, battery) housed in a capsule made of inert materials.

In other examples, fragile radio frequency identification (RFID) tags are used in drug ingestion monitoring applications. In order for the RFID tags to be operational, each requires an internal power supply. The RFID tags are antenna structures that are configured to transmit a radio-frequency signal through the body.

Among the many shortcomings of existing devices is that the power source is internal to device and such power sources are costly to produce and potentially harmful to the surrounding environment if the power source leaks or is damaged. Additionally, having antennas extending from the device is a concern as related to the antennas getting damaged or causing a problem when the device is used in-vivo.

SUMMARY

Enhanced ingestible event markers are provided. Aspects of the markers may include the presence of a matrix layer that includes a binder and source of an electron acceptor. Alternatively or in addition to the matrix layer, aspects of the markers may include a large surface area electrode having a surface area that exceeds the surface area of the circuitry of the marker. Aspects further include methods of making and using the ingestible event markers.

In some aspects, a system (e.g., event marker system) comprises a control device including a logic module, e.g., integrated circuit. First and second portions of a non-conductive membrane (skirt) are disposed on first and second sides, respectively, of the control device. A first material and a second material are electrically coupled to the logic module. The first and second materials are selected to provide a voltage potential difference as a result of the first and second materials being in contact with a conductive fluid, thus providing a source of power. The logic module is configured to control conductance between the first and second materials for producing a signal that is remotely detectable by a receiver. At least one of the first and second materials is disposed above or below at least one of the portions of the non-conductive membrane.

In some aspects, a system (e.g., event marker system) comprises a control device including a logic module. A first material is electrically coupled to the logic module, wherein the first material is an anode. A second material is electrically coupled to the logic module, wherein the second material is a cathode. An acidulating agent is disposed on a same side of the control device as the cathode. The first and second materials are selected to provide a voltage potential difference as a result of the first and second materials being in contact with a conductive fluid, thus providing a source of power. The logic module is configured to control conductance between the first and second materials for producing a signal that is remotely detectable by a receiver.

In some aspects, a system comprises a control device including a logic module. First and second portions of a non-conductive membrane (skirt) are disposed on first and second sides, respectively, of the control device. A first material is electrically coupled to the logic module, wherein at least a portion of the first material is disposed above the control device. A first layer of a second material is electrically coupled to the logic module, wherein the first layer is disposed below the control device. A third material, which is conductive, is coupled to the first layer of the second material. A second layer of the second material is electrically coupled to the first layer by the third material. The first and second materials are selected to provide a voltage potential difference as a result of the first material and the second layer of the second material being in contact with a conductive fluid, thus providing a source of power. The logic module is configured to control conductance between the first material and the second layer of the second material for producing a signal that is remotely detectable by a receiver.

DETAILED DESCRIPTION

Figure 1:
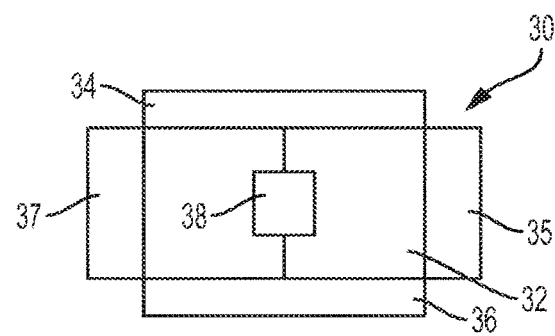
FIG. 1 is a block diagram representation of one aspect of an ingestible event marker with dissimilar metals positioned on opposite sides of a support that includes a circuitry component.

Enhanced ingestible event markers are provided. Aspects of the markers may include the presence of a matrix layer that includes a binder and source of an electron acceptor. Alternatively or in addition to the matrix layer, aspects of the markers may include a large surface area electrode having a surface area that exceeds the surface area of the circuitry of the marker. Aspects further include methods of making and using the ingestible event markers.

Ingestible Event Markers

As summarized above, aspects of the invention include improved ingestible event markers (IEMs). In describing various aspects, the ingestible event markers will be described first in general terms, followed by a detailed description of the matrix and high surface area electrode aspects which may be present in the ingestible event markers.

Ingestible event markers are ingestible devices. As the ingestible event markers are ingestible, they are configured to be ingested or swallowed, i.e., taken into the stomach by drawing through the throat and esophagus with a voluntary muscular action. Accordingly, the devices are dimensioned so as to be capable of being ingested. In some instances, the devices have a longest dimension of 30 mm or less, such as 20 mm or less, e.g., 10 mm or less, including 5 mm or less. The volume of the ingestible event marker may also vary so long as the composition is suitable for ingestion, where the volume in some instances may be 25 mm$^3$ or less, such as 15 mm$^3$ or less, including 10 mm$^3$ or less.

Ingestible event markers (i.e., IEM, also known as an ingestible event indicators) include an identifier circuitry component (also referred to herein as a controller or control device) and, optionally, a current path extender, e.g., a membrane, sometimes referred to herein as a "skirt". Various aspects of an IEM may include a control device for altering conductance; and a partial power source. The partial power source may include a first material electrically coupled to the control device; and a second material electrically coupled to the control device and electrically isolated from the first material, where the first and second materials are dissimilar.

Upon ingestion, the IEM contacts a conducting fluid, e.g., stomach fluid. When the IEM is in contact with the conducting liquid, a current path is formed through the conducting liquid between the first and second materials. The voltage potential created between the materials provides the power for operating the IEM as well as produces the current flow through the conducting fluid and the system. In one aspect, the IEM operates in direct current mode. In an alternative aspect, the IEM controls the direction of the current so that the direction of current is reversed in a cyclic manner, similar to alternating current. The current path through the system is controlled by the control device. Completion of the current path allows for the current to flow and in turn a receiver, not shown, can detect the presence of the current and recognize that the system has been activated and the desired event is occurring or has occurred.

In one aspect, the two materials are similar in function to the two electrodes needed for a direct current power source, such as a battery. The conducting liquid acts as the electrolyte needed to complete the power source. The completed power source is defined by the electrochemical reaction between the dissimilar materials of the IEM and the completion of the power source is enabled by the fluids of the body. The completed power source may be viewed as a power source that exploits electrochemical conduction in an ionic or a conducting solution such as gastric fluid, blood, or other bodily fluids and some tissues.

In certain aspects, the complete power source or supply is one that is made up of active electrode materials, electrolytes, and inactive materials, such as current collectors and packaging. The active materials are any pair of materials with different electrochemical potentials. Suitable materials are not restricted to metals, and in certain aspects the paired materials are chosen from metals and non-metals, e.g., a pair made up of a metal (such as Mg) and a salt (such as CuI). With respect to the active electrode materials, any pairing of substances—metals, salts, or intercalation compounds—with suitably different electrochemical potentials (voltage) and low interfacial resistance are suitable. Where desired, the voltage provided by the two dissimilar electrochemical materials upon contact of the materials of the power source with the target physiological site is 0.001 V or higher, including 0.01 V or higher, such as 0.1 V or higher, e.g., 0.3 V or higher, including 0.5 volts or higher, and including 1.0 volts or higher, where in certain aspects, the voltage ranges from about 0.001 to about 10 volts, such as from about 0.01 to about 10 V.

Anode materials of interest include, but are not limited to: magnesium, zinc, sodium, lithium, iron and alloys thereof, e.g., Al and Zn alloys of Mg, which may or may not be intercalated with a variety of materials such, as graphite with Li, K, Ca, Na, Mg, and the like. Cathode materials of interest include, but are not limited to, metallic salts, e.g., copper salts, such as copper salts of iodide, chloride, bromide, sulfate, formate, gluconate, Fe3+ salts, e.g., (such as iron sulfate, iron gluconate, iron citrate, iron phosphates (include iron orthophosphate and iron pyrophosphate) etc.), silver salts (such as AgCl, etc.); metals, e.g., gold, platinum, titanium, etc.; other conductive materials, e.g., graphite, etc., and the like. Where metals are employed, one or both of the metals may be doped with a non-metal, for example to enhance the voltage output of the battery. Non-metals that may be used as doping agents in certain aspects include, but are not limited to: sulfur, iodine and the like. In certain aspects, the electrode materials are cuprous iodine (CuI) or cuprous chloride (CuCl) as the anode and magnesium (Mg) metal or magnesium alloy as the cathode. Aspects of the present invention use electrode materials that are not harmful to the human body.

With respect to current signatures produced by the IEMs, the current signatures may distinguish one class of event indicator from other types or may be universally unique, such as where the current signature is analogous to a human fingerprint which is distinct from any other fingerprint of any other individual and therefore uniquely identifies an individual on a universal level. In various aspects, the control circuit may generate a variety of different types of communications, including but not limited to: RF signals, magnetic signals, conductive (near-field) signals, acoustic signals, etc.

In various aspects, the IEM may further include a current path extender, such as a membrane, which produces a virtual dipole length between the pair of dissimilar materials (functioning as transmission elements) that is longer than the actual dipole length. In addition to controlling the magnitude of the current path between the materials, such a membrane (sometimes referred to herein as "amplifier" or "skirt") is used to increase the "length" of the current path and, hence, act to boost the conductance path, as disclosed in the PCT application no. PCT/US2008/077753 published as WO2009/042812 and in U.S. Pat. No. 7,978,064, the entire contents of which are incorporated herein by reference. Throughout the disclosure herein, the terms "membrane", "skirt" and "amplifier" are used interchangeably with the term "current path extender" without impacting the scope or the present aspects and the claims herein.

Various aspects of IEMs of interest (including protocols for the fabrication thereof) are described in PCT Application Serial No. PCT/US2006/016370 published as WO/2006/116718; PCT Application Serial No. PCT/US2007/082563 published as WO/2008/052136; PCT Application Serial No. PCT/US2007/024225 published as WO/2008/063626; PCT Application Serial No. PCT/US2007/022257 published as WO/2008/066617; PCT Application Serial No. PCT/US2008/052845 published as WO/2008/095183; PCT Application Serial No. PCT/US2008/053999 published as WO/2008/101107; PCT Application Serial No. PCT/US2008/056296 published as WO/2008/112577; PCT Application Serial No. PCT/US2008/056299 published as WO/2008/112578; PCT Application Serial No. PCT/US2008/077753 published as WO2009/042812; PCT Application Serial No. PCT/US2008/085048 published as WO2009/070773; PCT Application Serial No. PCT/US2009/36231 published as WO2009/111664; PCT Application Serial No. PCT/US2009/049618 published as WO2010/005877; PCT Application Serial No. PCT/US2009/053721 published as WO2010/019778; PCT Application Serial No. PCT/US2009/060713 published as WO2010/045385; PCT Application Serial No. PCT/US2009/064472 published as WO2010/057049; PCT Application Serial No. PCT/US2009/067584 published as WO2010/068818; PCT Application Serial No. PCT/US2009/068128 published as WO2010/075115; PCT Application Serial No. PCT/US2010/020142 published as WO2010/080765; PCT Application Serial No. PCT/US2010/020140 published as WO2010/080764; PCT Application Serial No. PCT/US2010/020269 published as WO2010/080843; PCT Application Serial No. PCT/US2010/028518 published as WO2010/111403; PCT Application Serial No. PCT/US2010/032590 published as WO2010/129288; PCT Application Serial No. PCT/US2010/034186 published as WO2010/132331; PCT Application Serial No. PCT/US2010/055522 published as WO2011/057024; the disclosures of which are herein incorporated by reference.

In certain aspects, the ingestible IEMs are disrupted upon administration to a subject. As such, in certain aspects, the compositions are physically broken, e.g., dissolved, degraded, eroded, etc., following delivery to a body, e.g., via ingestion, injection, etc. The compositions of these aspects are distinguished from devices that are configured to be ingested and survive transit through the gastrointestinal tract substantially, if not completely, intact.

Where desired, an active agent (e.g., as described above) may be present in one or more of the IEM components, e.g., in the electrochemical materials, the support, the membrane, etc. Examples of such configurations are described in PCT Application Serial No. PCT/US2010/032590 published as WO2010/129288; the disclosures of which are herein incorporated by reference.

With reference to FIG. 1, there is shown one aspect of an ingestible device event indicator system with dissimilar metals positioned on opposite sides of system 30. The system 30 can be used in association with any pharmaceutical product, as mentioned above, and in one aspect, to determine when a patient takes the pharmaceutical product. The scope of the present invention is not limited by the environment and the product that is used with the system 30. For example, the system 30 may be placed within a capsule and the capsule is placed within the conducting liquid. The capsule would then dissolve over a period of time and release the system 30 into the conducting liquid. Thus, in one aspect, the capsule would contain the system 30 and no product. Such a capsule may then be used in any environment where a conducting liquid is present and with any product. For example, the capsule may be dropped into a container filled with jet fuel, salt water, tomato sauce, motor oil, or any similar product. Additionally, the capsule containing the system 30 may be ingested at the same time that any pharmaceutical product is ingested in order to record the occurrence of the event, such as when the product was taken.

In the specific example of the system 30 combined with the pharmaceutical product, as the product or pill is ingested, the system 30 is activated. The system 30 controls conductance to produce a unique current signature that is detected, thereby signifying that the pharmaceutical product has been taken. In other aspects, the current signature may contain information on the ingredients of the ingested pharmaceutical product which may include their chemical composition, date of manufacture, batch number, etc., among other desired information related to the pharmaceutical product which may be a placebo as well. The system 30 includes a framework 32. The framework 32 is a chassis for the system 30 and multiple components are attached to, deposited upon, or secured to the framework 32. In this aspect of the system 30, a digestible material 34 is physically associated with the framework 32. The material 34 may be chemically deposited on, evaporated onto, secured to, or built-up on the framework all of which may be referred to herein as "deposit" with respect to the framework 32. The material 34 is deposited on one side of the framework 32. The materials of interest that can be used as material 34 include, but are not limited to those described above. The material 34 is deposited by using any convenience protocol, including but not limited to physical vapor deposition, electro-deposition, or plasma deposition, liquid deposition, among other protocols. The material 34 may be from about 0.05 to about 500 µm thick, such as from about 5 to about 100 µm thick. The shape may be controlled by shadow mask deposition, or photolithography and etching. Additionally, even though only one region is shown for depositing the material, each system 30 may contain two or more electrically unique regions where the material 34 may be deposited, as desired. It should be noted that while the electrode materials described in connection with FIG. 1 are discussed above in terms of a particular fabrication protocol, they may be fabricated using other protocols, such as the laminate or printing protocols described in greater detail below in connection with the discussion of large surface area electrodes.

Figure 2:
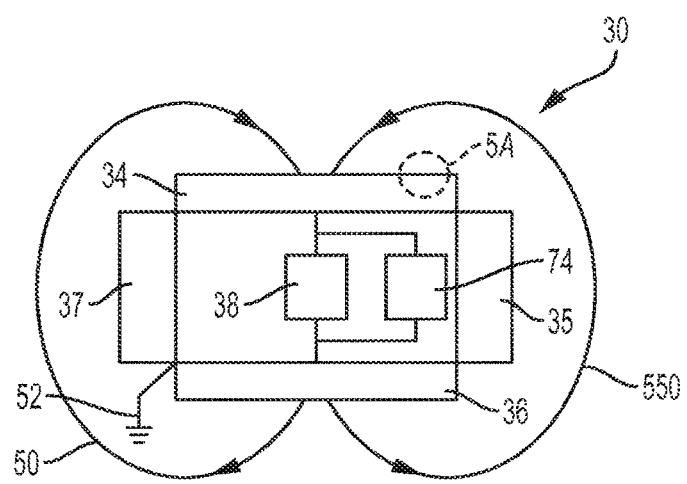
FIG. 2 shows ionic transfer or the current path through a conducting fluid when the event indicator system of an ingestible event indicator is in contact with conducting liquid and in an active state.

At a different side, which may be the opposite side as shown in FIG. 2, another digestible material 36, electrically isolated from the material 34, is deposited, such that materials 34 and 36 are dissimilar. Although not shown, the different side selected may be the side next to the side selected for the material 34. The scope of the present invention is not limited by the side selected and the term "different side" can mean any of the multiple sides that are different from the first selected side. Furthermore, even though the shape of the system is shown as a square, the shape may be any geometrically suitable shape. Materials 34 and 36 are selected such that they produce a voltage potential difference when the system 30 is in contact with conducting liquid, such as body fluids. The materials of interest for material 36 include, but are not limited to: Mg, Zn, or other electronegative metals, e.g., as described above. As indicated above with respect to the material 34, the material 36 may be chemically deposited on, evaporated onto, secured to, or built-up on the framework. Also, an adhesion layer may be employed, as convenient, to help the material 36 (as well as material 34 when needed) to adhere to the framework 32. Adhesion layers of interest for the material 36 are Ti, TiW, Cr or similar material. Anode material and the adhesion layer may be deposited by physical vapor deposition, electro-deposition or plasma deposition, where desired. The material 36 may be from about 0.05 to about 500 µm thick, such as from about 5 to about 100 µm thick. However, the scope of the present invention is not limited by the thickness of any of the materials nor by the type of process used to deposit or secure the materials to the framework 32.

Thus, when the system 30 is in contact with the conducting fluid, e.g., a liquid, a current path, an example is shown in FIG. 2, is formed through the conducting liquid between material 34 and 36. A control device 38 is secured to the framework 32 and electrically coupled to the materials 34 and 36. The control device 38 includes electronic circuitry, for example, a memory, a control logic that is capable of controlling and altering the conductance between the materials 34 and 36.

The voltage potential created between the materials 34 and 36 provides the power for operating the system as well as produces the current flow through the conducting fluid and the system. In one aspect, the system operates in direct current mode. In an alternative aspect, the system controls the direction of the current so that the direction of current is reversed in a cyclic manner, similar to alternating current. As the system reaches the conducting fluid or the electrolyte, where the fluid or electrolyte component is provided by a physiological fluid, e.g., stomach acid, the path for current flow between the materials 34 and 36 is completed external to the system 230; the current path through the system 30 is controlled by the control device 38. Completion of the current path allows for the current to flow, through conductive communication through the stomach, and in turn to a receiver, not shown, the receiver capable of detecting the presence of the current signature containing information and further recognize that the system 30 has been activated and the desired event is occurring or has occurred.

In one aspect, the two materials 34 and 36 are similar in function to the two electrodes needed for a direct current power source, such as a battery. The conducting liquid acts as the electrolyte needed to complete the power source. The completed power source described is defined by the physical chemical reaction between the materials 34 and 36 of the system 30 and the surrounding fluids of the body. The completed power source may be viewed as a power source that exploits reverse electrolysis in an ionic or a conductive solution such as gastric fluid, blood, or other bodily fluids and some tissues. Additionally, the environment may be something other than a body and the liquid may be any conducting liquid. For example, the conducting fluid may be salt water or a metallic based paint.

Referring again to FIG. 1, the materials 34 and 36 provide the voltage potential to activate the control device 38. Once the control device 38 is activated or powered up, the control device 38 can alter conductance between the materials 34 and 36 in a unique or desired manner. By altering the conductance between materials 34 and 236, the control device 38 is capable of controlling the magnitude of the current through the conducting liquid that surrounds the system 30. This produces a unique current signature that can be detected and measured by a receiver (not shown), which can be positioned internal, over or external to the body.

As described above, in various aspects, the event indicator may further include a current path extender such as a membrane which, for example, produces a virtual dipole length between the pair of transmission elements that is larger than the actual dipole length. As illustrated in FIG. 1, the current path extender or "skirt", shown in portion at 35 and 37, respectively, may be associated with, e.g., secured to, the framework 32. Various shapes and configurations for the skirt are contemplated as within the scope of the present invention. For example, the system 30 may be surrounded entirely or partially by the skirt and the skirt may be positioned along a central axis of the system 30 or off-center relative to a central axis. Thus, the scope of the present invention as claimed herein is not limited by the shape or size of the skirt. Furthermore, in other aspects, the materials 34 and 36 may be separated by one skirt that is positioned in any defined region between the materials 34 and 36.

Figure 3A:
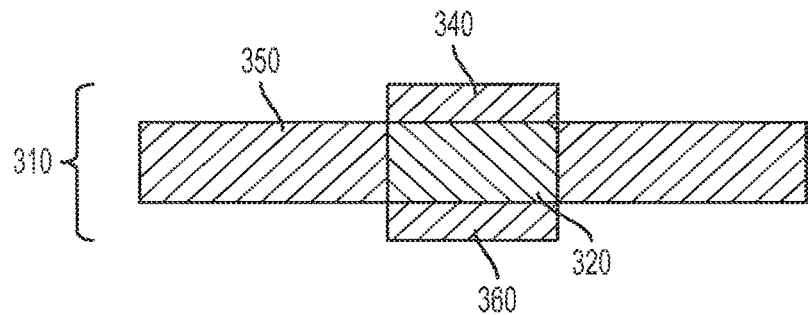
FIGS. 3A and 3B provide side and top views, respectively, of one aspect of an ingestible event indicator.
Figure 3B:
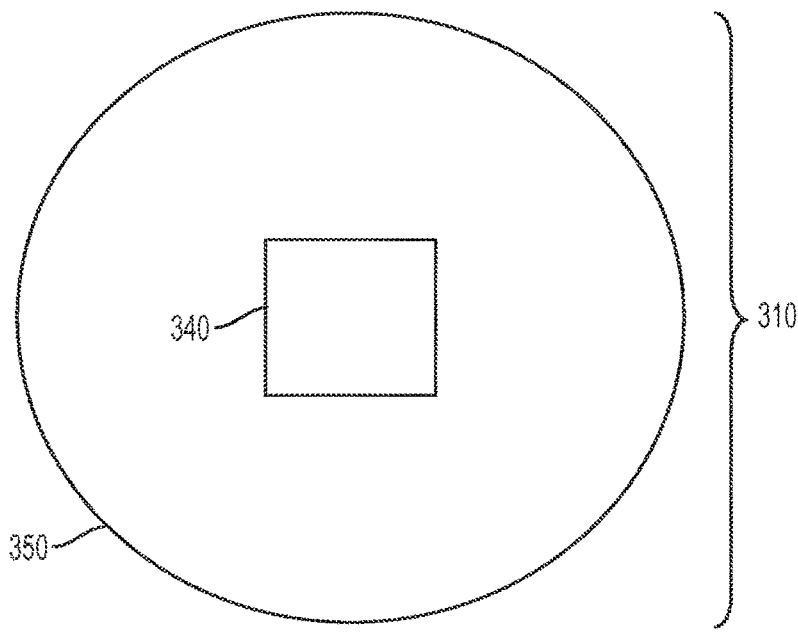

FIG. 3A provides a view of an aspect of an IEM of interest which has a current path extender in the form of a membrane that extends beyond the outer edges of the signal transmission elements to provide a virtual dipole having a length that is longer than the actual dipole between the signal transmission elements. As shown in FIG. 3A, event indicator 310 includes integrated circuit 320, having a first electrochemical material 340 (which may comprise two distinct material layers) and a second electrochemical material 360. Also shown is disc-shaped membrane 350. FIG. 3B provides an overhead view of the event indicator shown in FIG. 3A, showing the disc shape of first electrochemical material 340 and the positioning of the first electrochemical material in the center of disc-shaped membrane 350. The distance that the edge of the membrane may extend beyond the edge of electrodes may vary, and in certain aspects is 0.05 mm or more, e.g., 0.1 mm or more, including 1.0 mm or more, such as 5.0 mm or more and including 10 mm or more, where the distance may not exceed 100 mm in certain aspects.

As can be seen in the aspect depicted in FIGS. 3A & 3B, the first and second electrochemical materials may have any convenient shape, e.g., square, disc, etc. The disc-shaped membrane 350 is a planar disc structure, where the edge of the membrane extends beyond the edge of the first and second electrochemical materials. In the depicted aspect, the radius of the membrane is longer than the radius of the first and second electrochemical materials, e.g., by 1 mm or more, such as by 10 mm or more. Membranes may have "two-dimensional" or "three-dimensional" configurations, as desired. Membrane configurations of interest are further described in PCT Application Serial No. PCT/US2008/077753 published as WO2009/042812, PCT Application Serial No. PCT/US2010/020142 published as WO2010/080765 as well as PCT Application Serial No. PCT/US2010/032590 published as WO2010/129288; the disclosures of which are herein incorporated by reference. The membrane may be fabricated from a number of different materials, where the membrane may be made of a single material or be a composite of two or more different types of materials, as developed in greater detail below. Where desired, the membrane may be made up partially or completely of a highly-swellable polymeric film, e.g., as described in U.S. Provisional Application Ser. No. 61/758,030 filed on Jan. 29, 2013, the disclosure of which is herein incorporated by reference. In such instances, the highly-swellable polymeric film is associated with the support and is configured as a signal amplification that increases a length of a current path between the first and second materials. In certain instances, the membrane will have a mechanical strength sufficient to withstand the mechanical forces typical of the gastrointestinal (GI) tract without folding onto itself and losing its shape. This desired mechanical strength may be chosen to last for at least the duration of the communication, which may be 1 second or longer, such as at least 1 minute or longer, up to 6 hours or longer. In certain aspects, the desired mechanical strength is selected to last at least for a period of time ranging from 1 to 30 minutes. The desired mechanical strength can be achieved by proper selection of polymer and/or fillers, or mechanical design (e.g., lamination of multiple layers, or curvature of the amplifier surface) to increase the mechanical strength of the final structure. Membranes of the invention are ones that are electrically insulating. As such, the materials from which the membranes are fabricated are electrically insulating materials. A given material is electrically insulating if it has a resistivity that is two times or greater than the medium in which the device operates, e.g., stomach fluid, such as ten times or greater, including 100 times or greater than the medium in which the device operates.

Figure 4:
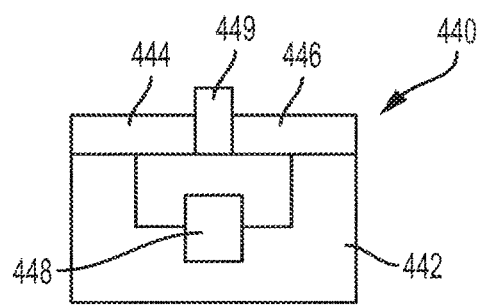
FIG. 4 is a block diagram representation of another aspect of the event indicator system with dissimilar metals positioned on the same end and separated by a non-conducting material.

Referring now to FIG. 4, in another aspect of an ingestible device is shown in more detail as system 440. The system 440 includes a framework 442. The framework 442 is similar to the framework 32 of FIG. 1. In this aspect of the system 440, a digestible or dissolvable material 444 is deposited on a portion of one side of the framework 442. At a different portion of the same side of the framework 442, another digestible material 446 is deposited, such that materials 444 and 446 are dissimilar. More specifically, material 444 and 446 are selected such that they form a voltage potential difference when in contact with a conducting liquid, such as body fluids. Thus, when the system 440 is in contact with and/or partially in contact with the conducting liquid, then a current path, an example is shown in FIG. 2, is formed through the conducting liquid between material 444 and 446. A control device 448 is secured to the framework 442 and electrically coupled to the materials 444 and 446. The control device 448 includes electronic circuitry that is capable of controlling part of the conductance path between the materials 444 and 446. The materials 444 and 446 are separated by a non-conducting skirt 449. Various examples of the skirt 449 are disclosed in PCT Application No. PCT/US2010/032590 published as WO2010/129288; and PCT application Ser. No. PCT/US2008/077753 published as WO2009/042812; the entire disclosure of each is incorporated herein by reference. Once the control device 448 is activated or powered up, the control device 448 can alter conductance between the materials 444 and 446. Thus, the control device 448 is capable of controlling the magnitude of the current through the conducting liquid that surrounds the system 440. As indicated above with respect to system 30, a unique current signature that is associated with the system 440 can be detected by a receiver (not shown) to mark the activation of the system 440. In order to increase the "length" of the current path the size of the skirt 449 is altered. The longer the current path, the easier it may be for the receiver to detect the current.

Figure 2A:
FIG. 2A shows an exploded view of the surface of a dissimilar material as illustrated in FIG. 2.

Referring now to FIG. 2, the system 30 of FIG. 1 is shown in an activated state and in contact with conducting liquid. The system 30 is grounded through ground contact 52. The system 30 also includes a sensor module 74, which is described in greater detail with respect to FIG. 6. Ion or current paths 550 form between material 34 to material 36 through the conducting fluid in contact with the system 30. The voltage potential created between the material 34 and 36 is created through chemical reactions between materials 34/36 and the conducting fluid. FIG. 2A provides an exploded view of the surface of material 34. The surface of the material 34 is not planar, but rather an irregular surface 54 as shown. The irregular surface 54 increases the surface area of the material and, hence, the area that comes in contact with the conducting fluid. In one aspect, at the surface of the material 34, there is chemical reaction between the material 34 and the surrounding conducting fluid such that mass is released into the conducting fluid. The term "mass" as used herein refers to protons and neutrons that form a substance. One example includes where the material is CuCl and when in contact with the conducting fluid, CuCl becomes Cu (solid) and Cl$^-$ in solution. The flow of ions into the conduction fluid is depicted by the ion paths 50. In a similar manner, there is a chemical reaction between the material 36 and the surrounding conducting fluid and ions are captured by the material 36. The release of ions at the material 34 and capture of ion by the material 36 is collectively referred to as the ionic exchange. The rate of ionic exchange and, hence the ionic emission rate or flow, is controlled by the control device 38. The control device 38 can increase or decrease the rate of ion flow by altering the conductance, which alters the impedance, between the materials 34 and 36. Through controlling the ion exchange, the system 30 can encode information in the ionic exchange process. Thus, the system 30 uses ionic emission to encode information in the ionic exchange.

The control device 38 can vary the duration of a fixed ionic exchange rate or current flow magnitude while keeping the rate or magnitude near constant, similar to when the frequency is modulated and the amplitude is constant. Also, the control device 38 can vary the level of the ionic exchange rate or the magnitude of the current flow while keeping the duration near constant. Thus, using various combinations of changes in duration and altering the rate or magnitude, the control device 38 encodes information in the current flow or the ionic exchange. For example, the control device 38 may use, but is not limited to any of the following techniques namely, Binary Phase-Shift Keying (PSK), Frequency modulation, Amplitude modulation, on-off keying, and PSK with on-off keying.

As indicated above, the various aspects disclosed herein, such as systems 30 and 440 of FIGS. 1 and 4, respectively, include electronic components as part of the control device 38 or the control device 448. Components that may be present include but are not limited to: logic and/or memory elements, an integrated circuit, an inductor, a resistor, and sensors for measuring various parameters. Each component may be secured to the framework and/or to another component. The components on the surface of the support may be laid out in any convenient configuration. Where two or more components are present on the surface of the solid support, interconnects may be provided.

As indicated above, the system, such as system 30 and 440, control the conductance between the dissimilar materials and, hence, the rate of ionic exchange or the current flow. Through altering the conductance in a specific manner the system is capable of encoding information in the ionic exchange and the current signature. The ionic exchange or the current signature is used to uniquely identify the specific system. Additionally, the systems 30 and 440 are capable of producing various different unique exchanges or signatures and, thus, provide additional information. For example, a second current signature based on a second conductance alteration pattern may be used to provide additional information, which information may be related to the physical environment. To further illustrate, a first current signature may be a very low current state that maintains an oscillator on the chip and a second current signature may be a current state at least a factor of ten higher than the current state associated with the first current signature.

Figure 6:
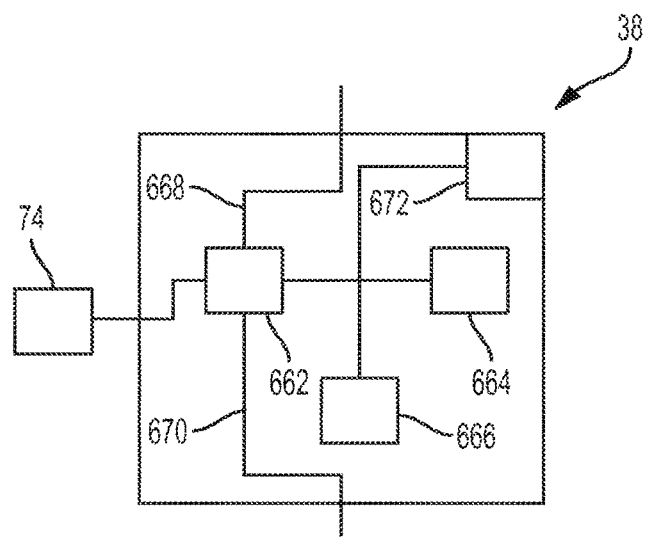
FIG. 6 is a block diagram illustration of one aspect of the control device used in the system of FIGS. 1, 2 and 4.

Referring now to FIG. 6, a block diagram representation of the control device 38 is shown. The device 38 includes a control module 662, a counter or clock 664, and a memory 666. Additionally, the device 38 is shown to include a sensor module 672 as well as the sensor module 74, which was referenced in FIG. 2. The control module 662 has an input 668 electrically coupled to the material 34 and an output 670 electrically coupled to the material 36. The control module 662, the clock 664, the memory 666, and the sensor modules 672/274 also have power inputs (some not shown). The power for each of these components is supplied by the voltage potential produced by the chemical reaction between materials 34 and 36 and the conducting fluid, when the system 30 is in contact with the conducting fluid. The control module 662 controls the conductance through logic that alters the overall impedance of the system 30. The control module 662 is electrically coupled to the clock 664. The clock 64 provides a clock cycle to the control module 662. Based upon the programmed characteristics of the control module 662, when a set number of clock cycles have passed, the control module 662 alters the conductance characteristics between materials 34 and 36. This cycle is repeated and thereby the control device 38 produces a unique current signature characteristic. The control module 662 is also electrically coupled to the memory 666. Both the clock 664 and the memory 666 are powered by the voltage potential created between the materials 34 and 36.

The control module 662 is also electrically coupled to and in communication with the sensor modules 672 and 274. In the aspect shown, the sensor module 672 is part of the control device 38 and the sensor module 74 is a separate component. In alternative aspects, either of the sensor modules, 672 and 74, can be used without the other and the scope of the present invention is not limited by the structural or functional location of the sensor modules 672 or 74. Additionally, any component of the system 30 may be functionally or structurally moved, combined, or repositioned without limiting the scope of the present invention as claimed. Thus, it is possible to have one single structure, for example a processor, which is designed to perform the functions of all of the following modules: the control module 662, the clock 664, the memory 666, and the sensor module 672 or 274. On the other hand, it is also within the scope of the present invention to have each of these functional components located in independent structures that are linked electrically and able to communicate.

Referring again to FIG. 6, the sensor modules 672 or 274 can include any of the following sensors: temperature, pressure, pH level, and conductivity. In one aspect, the sensor modules 672 or 74 gather information from the environment and communicate the analog information to the control module 662. The control module then converts the analog information to digital information and the digital information is encoded in the current flow or the rate of the transfer of mass that produces the ionic flow. In another aspect, the sensor modules 672 or 74 gather information from the environment and convert the analog information to digital information and then communicate the digital information to control module 662. In the aspect shown in FIG. 2, the sensor module 74 is shown as being electrically coupled to the materials 34 and 36 as well as the control device 38. In another aspect, as shown in FIG. 6, the sensor module 74 is electrically coupled to the control device 38 at connection 678. The connection 678 acts as both a source for power supply to the sensor module 74 and as a communication channel between the sensor module 74 and the control device 38.

Figure 5:
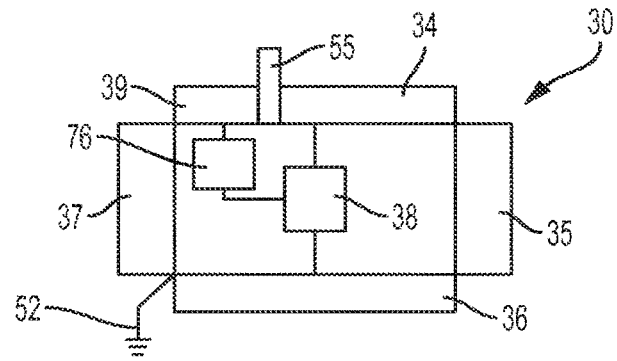
FIG. 5 shows the event indicator system of FIG. 2 with a pH sensor unit.

Referring now to FIG. 5, the system 30 includes a pH sensor module 76 connected to a material 39, which is selected in accordance with the specific type of sensing function being performed. The pH sensor module 76 is also connected to the control device 38. The material 39 is electrically isolated from the material 34 by a non-conductive barrier 55. In one aspect, the material 39 is platinum. In operation, the pH sensor module 76 uses the voltage potential difference between the materials 234/236. The pH sensor module 76 measures the voltage potential difference between the material 34 and the material 39 and records that value for later comparison. The pH sensor module 76 also measures the voltage potential difference between the material 39 and the material 36 and records that value for later comparison. The pH sensor module 76 calculates the pH level of the surrounding environment using the voltage potential values. The pH sensor module 76 provides that information to the control device 38. The control device 38 varies the rate of the transfer of mass that produces the ionic transfer and the current flow to encode the information relevant to the pH level in the ionic transfer, which can be detected by a receiver (not shown). Thus, the system 30 can determine and provide the information related to the pH level to a source external to the environment.

As indicated above, the control device 38 can be programmed in advance to output a pre-defined current signature. In another aspect, the system can include a receiver system that can receive programming information when the system is activated. In another aspect, not shown, the switch 664 and the memory 666 can be combined into one device.

In addition to the above components, the system 30 may also include one or other electronic components. Electrical components of interest include, but are not limited to: additional logic and/or memory elements, e.g., in the form of an integrated circuit; a power regulation device, e.g., battery, fuel cell or capacitor; a sensor, a stimulator, etc.; a signal transmission element, e.g., in the form of an antenna, electrode, coil, etc.; a passive element, e.g., an inductor, resistor, etc.

The above description provides a general review of various aspects of IEMs. As summarized above, aspects of the improved IEMs of the present disclosure include at least one of: a matrix layer that includes a binder and an electron acceptor; and an electrode having a surface area that exceeds the surface area of the circuitry of the marker. Each of these aspects is now described in greater detail below.

Matrix Layer that Includes a Binder and Source of an Electron Acceptor

Where desired, an IEM may have a matrix layer that includes a source of an electron acceptor and a binder, i.e., an electron acceptor source matrix layer. The matrix layer is a material structure, e.g., in the form of a film or coating, which is a component of the IEM. While the dimensions of the matrix layer may vary, in some instances the layer has a thickness of 10 microns or greater, such as 50 microns or greater, including 100 microns or greater, and ranges in thickness in some instances from 10 to 1000, such as 20 to 200 and including 30 to 60 microns. The top and bottom surfaces of the layer may have a variety of different configurations, including but not limited to rectangular, trapezoidal, triangular, etc.; curvilinear, such as circular, ovoid or other curvilinear shape, etc. Where the layer has a surface which may be defined by length and width, these dimensions may vary, where in some instances the length ranges from 1 to 20, such as 2 to 10 and including 3 to 6 mm and the width ranges from 1 to 20, such as 2 to 10 and including 3 to 6 mm. A matrix layer, when present, may be stably associated with the cathode material of the IEM. By "stably associated" is meant that the matrix layer and cathode do not separate from each other, at least until after the IEM has performed its intended function.

As summarized above, matrix layers of interest include a source of an electron acceptor (i.e., an electron acceptor source) present in a binder. In other words, the source of the electron acceptor is dispersed in or distributed throughout the binder, or at least a portion thereof, such as 10% or more of the binder, e.g., 20% or more, 25% or more, 50% or more, 75% or more, including 90% or more of the binder. The source of the electron acceptor is a component, which may be a distinct compound from the binder material or a functional moiety of the binder material, and can serve as a source of hydrogen ions upon contact with an aqueous medium. The hydrogen ions produced upon contact with an aqueous medium are then reduced to $H_2$ at the cathode surface.

In some instances, the electron acceptor source is an acidulant. The term "acidulant" refers to a compound that dissolves upon contact with an aqueous medium to produce hydrogen ions. Acidulants of interest include both polymeric and non-polymeric compounds, where the compounds may be organic or inorganic, so long as the acidulant is suitable for ingestion, i.e., is non-toxic, at least in the amounts present in the IEM. Acidulants of interest include, but are not limited to: organic acids, such as glycolic acid, lactic acid, methyl lactic acid, polycarboxylic acids, e.g., malic acid, citric acid, tartronic acid, tartaric acid, succinic acid, etc.; anionic polymers, i.e., polymers that include monomeric units having an acidic functional group, such as a carboxyl, sulfate, sulfonate, phosphate or phosphonate groups; etc. Suitable anionic polymers include alginates, e.g., alginic acid and salts thereof, polyacrylic acid, dextran sulfate, carboxymethylcellulose, hyaluronic acid, polyglucuronic acid, polymanuronic acid, polygalacturonic acid, polyarabinic acid; chrondroitin sulfate and dextran phosphate. Suitable cationic polymers include chitosan, polyethylenimine, poly-L-lysine, and dimethylaminodextran. Of interest in some instances are polysaccharide anionic polymers. Polysaccharide anionic polymers of interest include alginates, e.g., alginic acid and salts thereof. Alginic acid (i.e., alginate) is a linear copolymer with homopolymeric blocks of (1-4)-linked β-D-mannuronate (M) residues and α-L-guluronate (G) residues. The residues are covalently linked together in different sequences or blocks. The residues can appear in homopolymeric blocks of consecutive G-residues (G-blocks), consecutive M-residues (M-blocks) or alternating M and G-residues (MG-blocks). Also of interest are salts of alginic acid, e.g., sodium alginate, calcium alginate, potassium alginate, etc. The molecular weight of the alginate (e.g., alginic acid or alginate salt thereof) may vary, ranging in some instances from 10,000 to 600,000 Daltons, such as 50,000 to 100,000 Daltons. When present, the amount of the acidulant may vary, and may range in some instances from 0.01 to 50, such as 0.1 to 25 and including 0.1 to 15 dry weight % of the matrix layer.

In addition to the electron acceptor, the matrix layer also includes a binder. The binder is a component of the matrix layer which may be made up of a single material or two or more different materials. Any material (or combination of materials) may be employed as the binder so long as the material(s) is ingestible (e.g., as described above) and functions to keep other components of the matrix, e.g., the acidulant, near the cathode surface when the IEM contacts an aqueous medium. Materials of interest for the binder include pharmaceutically acceptable polymeric materials, including but not limited to, cellulosic materials, such as ethyl cellulose, cellulose acetate phthalate, cellulose acetate trimaletate, hydroxy propyl methylcellulose phthalate, polyvinyl acetate phthalate, polyvinyl alcohol phthalate, shellac; hydrogels and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, ethyl cellulose, gelatin, starch, and cellulose based cross-linked polymers in which the degree of crosslinking is low so as to facilitate adsorption of water and expansion of the polymer matrix, hydroxypropyl cellulose, hydroxypropyl methylcellulose, polyvinylpyrrolidone, crosslinked starch, microcrystalline cellulose, chitin, pullulan, collagen, casein, agar, gum arabic, sodium carboxymethyl cellulose, (swellable hydrophilic polymers) poly(hydroxyalkyl methacrylate) (molecular weight 5 k to 5000 k), polyvinylpyrrolidone (molecular weight 10 k to 360 k), anionic and cationic hydrogels, zein, polyvinyl alcohol having a low acetate residual, a swellable mixture of agar and carboxymethyl cellulose, copolymers of maleic anhydride and styrene, ethylene, propylene or isobutylene, pectin (molecular weight 30 k to 300 k), polysaccharides such as agar, acacia, karaya, tragacanth, algins and guar, polyethylene oxides (molecular weight 100 k to 5000 k), diesters of polyglucan, crosslinked polyvinyl alcohol and poly N-vinyl-2-pyrrolidone, hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, methyl ethyl cellulose, ethylhydroxy ethylcellulose, cellulose acetate, cellulose butyrate, cellulose propionate, gelatin, starch, maltodextrin, pullulan, polyvinyl pyrrolidone, polyvinyl alcohol, polyvinyl acetate, glycerol fatty acid esters, natural gums, lecithins, pectin, alginates, ammonia alginate, sodium, calcium, potassium alginates, propylene glycol alginate, agar, and gums such as arabic, karaya, locust bean, tragacanth, carrageens, guar, xanthan, scleroglucan and mixtures and blends thereof, pharmaceutically acceptable acrylic polymers, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers, etc. Of interest are in some instances are polysaccharides, e.g., sodium alginate, sodium carboxymethyl cellulose, etc.

In addition to the binder and electron acceptor, the matrix may further include a surfactant agent (i.e., a wetting agent). The term "surfactant" is employed in its conventional sense to refer to a compound that reduces the surface tension of a liquid, causing the liquid to spread across or penetrate more easily the surface of a solid. Surfactants of interest include pharmaceutically acceptable anionic surfactants, cationic surfactants, amphoteric (amphipathic/amphiphilic) surfactants, and non-ionic surfactants. Suitable pharmaceutically acceptable anionic surfactants include, for example, monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, and alkyl sulfates. Suitable pharmaceutically acceptable non-ionic surfactants include, for example, polyoxyethylene compounds, lecithin, ethoxylated alcohols, ethoxylated esters, ethoxylated amides, polyoxypropylene compounds, propoxylate alcohols, ethoxylated/propoxylated block polymers, and propoxylated esters, alkanolamides, amine oxides, fatty acid esters of polyhydric alcohols, ethylene glycol esters, diethylene glycol esters, propylene glycol esters, glyceryl esters, polyglyceryl fatty acid esters, SPAN's (e.g., sorbitan esters), TWEEN's sucrose esters, and glucose (dextrose) esters. When present, the amount of the surfactant may vary, and may range in some instances from 0.01 to 25, such as 0.1 to 15 and including 0.01 to 10 dry weight % of the matrix layer.

In some instances, the matrix layer may further include a conductivity enhancer. A conductivity enhancer is a material (or combination of materials) that enhances conductivity of the layer upon contact with an aqueous medium. Examples of such components include pore forming agents (i.e., porogens). The term "porogen" as used herein, refers to a chemical compound that is included in the film and, upon contact with an aqueous medium, is removed from the film, e.g., via diffusion, dissolution, and/or degradation, to leave a pore in the resultant film. The diameter of the pores produced by the porogen may vary, ranging in some instances from 1 to 1000 μm, such as 1 to 500 μm and including 1 to 250 μm. Porogens of interest include both inorganic and organic porogens. Inorganic porogens of interest include, but are not limited to: inorganic salts, e.g., NaCl, $MgCl_2$, $CaCl_2$, $NH_4Cl$, $NH_4PO_4$, $NH_4CO_3$; soluble biocompatible salts; sugars (e.g., sugar alcohols), polysaccharides (e.g., dextran (poly(dextrose)), water soluble small molecules, natural or synthetic polymers, oligomers, or monomers that are water soluble or degrade quickly under physiological conditions, including but not limited to: polyethylene glycol, polyvinyl alcohol, poly(vinylpyrollidone), pullulan, poly(glycolide), poly(lactide), poly(lactide-co-glycolide), other polyesters, and starches. When present, the total amount of porogen component made up of one or more porogens may vary. In some instances, the amount of porogen component may range from 1 to 40, including from 5 to 10 dry weight percent of the layer.

Another type of conductivity enhancer that may be present in the matrix layer is conductive particle conductive enhancers. Such conductivity enhancers include particles made up of a conductive material. Conductive materials of interest include, but are not limited to, metals, e.g., gold, silver, etc., graphite, etc. While the dimensions of such particles may vary, in some instances the particles have a diameter ranging from 0.1 to 1000 microns, such as 1 to 500 microns, including 1 to 100 microns. When present in the matrix layer, the amount of the particles may range from 1 to 40, including 5 to 10 dry weight percent of the layer.

In some instances, a buffering agent may also be present in the matrix layer. Any convenient buffering agent may be employed, where a suitable buffering agent will be selected based on the pH level in the layer that is desired. Examples of buffering agents of interest include, but are not limited to: alkali earth metal buffering agent, a calcium buffering agent, a magnesium buffering agent, and an aluminum buffering, sodium bicarbonate, potassium bicarbonate, magnesium hydroxide, magnesium lactate, magnesium gluconate, magnesium oxide, magnesium aluminate, magnesium carbonate, magnesium silicate, magnesium citrate, aluminum hydroxide, aluminum phosphate, aluminum hydroxide/magnesium carbonate, potassium carbonate, potassium citrate, aluminum hydroxide/sodium bicarbonate coprecipitate, aluminum glycinate, aluminum magnesium hydroxide, sodium citrate, sodium tartrate, sodium acetate, sodium carbonate, sodium (polyphosphate, sodium dihydrogen phosphate, potassium polyphosphate, sodium pyrophosphate, potassium pyrophosphate, disodium hydrogenphosphate, dipotassium hydrogenphosphate, trisodium phosphate, tripotassium phosphate, potassium metaphosphate, calcium acetate, calcium glycerophosphate, calcium chloride, calcium hydroxide, calcium lactate, calcium carbonate, calcium gluconate, calcium bicarbonate, calcium citrate, calcium phosphate magnesium phosphate, potassium phosphate, sodium phosphate, trihydroxymethylaminomethane, an amino acid, an acid salt of an amino acid, an alkali salt of an amino acid, and combinations of any of the foregoing. When present in the matrix layer, the amount of the buffering agent may range from 0.1 to 25, including 0.1 to 15 dry weight percent of the layer.

Figure 7:
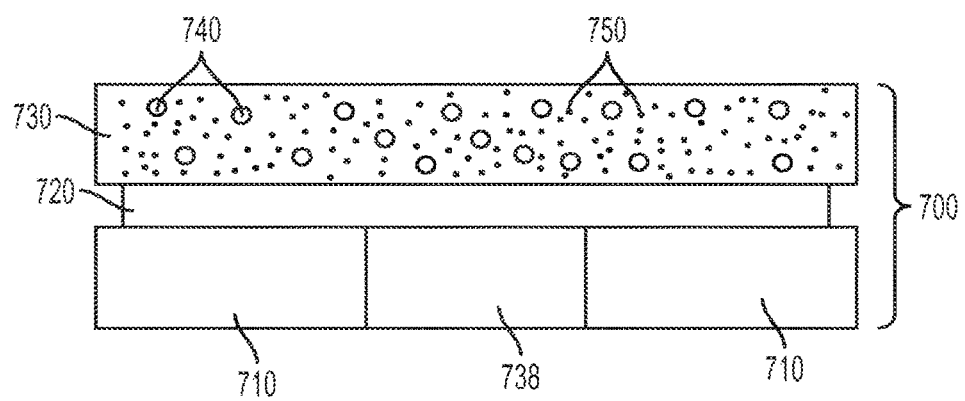
FIG. 7 provides a view of an IEM that includes a matrix layer, according to one aspect.

An example of an IEM which includes a matrix layer as described above is depicted in FIG. 7. As shown in FIG. 7, IEM 700 includes a control element 738 surrounded by a current amplifier 710. Present on the upper surface of control element 738 is cathode 720. Stably associated with cathode 720 is matrix layer 730 which includes acidulent 750 dispersed throughout a polymeric binder. Also shown are gold particles 740 which enhance the conductivity of the layer.

With respect to cathode layer 720, this can be fabricated from any convenient material, including the materials described above. As such, cathode materials of interest include, but are not limited to, metallic salts, e.g., copper salts, such as copper salts of iodide, chloride, bromide, sulfate, formate, gluconate, $Fe^{3+}$ salts, e.g., (such as iron sulfate, iron gluconate, iron citrate, iron phosphates (include iron orthophosphate and iron pyrophosphate) etc.), silver salts (such as AgCl, etc.); metals, e.g., gold, platinum, titanium, etc.; other conductive materials, e.g., graphite, etc., and the like. In some instances, the cathode is copper-free, meaning that copper is not present in the cathode. Examples of cathode materials in such instances include, but are not limited to: gold, platinum, graphite, iron salts, silver salts, etc. Copper-free cathodes may have a number of advantages as compared to cathodes which include copper, including but not limited to improved acceptance by the body, better storage stability, etc.

Also provided are methods of manufacturing IEMs that include an electron acceptor source matrix layer. Aspects of the methods include combining an IEM and matrix layer, e.g., as described above, in a manner sufficient such that the matrix layer is stably associated with an electrode, e.g., the cathode, of the IEM. Any convenient manufacturing protocol may be employed, where protocols of interest include both manual and automated protocols, as well as protocols that include both manual and automated steps. Protocols of interest that find use in various aspects of the fabrication methods described herein include lamination, molding, pressing, extrusion, stamping, coating (such as spray coating and dipping), gluing, etc. In some instances, fabrication protocols as described in PCT application serial nos. PCT/US2010/020142 published as WO 2010/080765; PCT/US2006/016370 published as WO 2006/116718 and PCT/US2008/077753 published as WO2009/042812 (the disclosures of which applications are herein incorporated by reference); are employed. By "stably associating" is meant that the IEM component and matrix component do not separate from each other, at least until desired during intended use, e.g., following passage into the intestine of a subject. Any convenient approach for stably associating the components may be employed.

Where an ingestible event marker with a matrix layer stably associated with a cathode is desired, e.g., as illustrated in FIG. 7, a protocol employing a pre-fabricated matrix layer may be used. In such a protocol, a dissimilar material of the ingestible event marker may be contacted with a pre-fabricated matrix layer in a manner sufficient to cover the dissimilar material with the film. Where desired, an adhesive may be employed to secure the components together.

In a variation of the above protocol, a fabrication process may be one in which the matrix layer is fabricated at the same time that the cathode component of the IEM is stably associated therewith. For example, a molding process may be employed where liquid matrix layer precursor composition is positioned in a mold, followed by placement of an ingestible component (e.g., IEM) on the precursor material. The solvent component of the liquid composition may be removed to associate the matrix layer with the dissimilar material of the ingestible event marker. Temperature modulation may be employed where appropriate. Following solidification of the precursor material, the resultant final product may be removed from the mold.

In yet another fabrication protocol of interest, a coating process may be employed to stably associate the ingestible component with the matrix layer component. For example, a premade IEM be provided, e.g., as described in in PCT application serial nos. PCT/US2010/020142 published as WO 2010/080765; PCT/US2006/016370 published as WO 2006/116718 and PCT/US2008/077753 published as WO2009/042812; the disclosures of which applications are herein incorporated by reference. This premade IEM may then be spray coated with a liquid precursor composition of the matrix layer. Following spray coating, the coating material may be allowed to produce the desired product.

Where desired, aspects of the above described or other suitable protocols may be combined to produce a fabrication protocol. For example, a molding process may be employed to make a product and the product spray coated with a further material, such as a soluble material.

Large Surface Area Electrodes

As summarized above, aspects may include IEMs with at least one large surface area electrode. Large surface area electrodes are electrodes having a surface area that exceeds the surface area of the side of the circuitry in the IEM with which the electrode is associated. While the dimensions of the large surface area electrode may vary, in some instances the dimensions are selected so that the electrode provides an enhanced amplitude of the change in conductance (as compared to an IEM in which the electrodes are commensurate is surface area with the surface area of the circuitry component), where the magnitude of the enhancement may be 1.2 or greater, such as 1.5 or greater, including 1.75 or greater, e.g., 2.0 or greater, 2.5 or greater, 3.0 or greater, etc. The difference in surface areas between the large surface area electrode and the surface area of the circuitry component with which the large surface area electrode is associated may vary, where the magnitude of the difference ranges, in some instances, from 1 to 15, such as 2 to 9 and including 3 to 8 $mm^2$. In some instances, the large surface area electrode has a surface area of 1.5 $mm^2$ or greater, including 2 $mm^2$ or greater, e.g., 4 $mm^2$ or greater, including 9 $mm^2$ or greater, where the surface area may range in some instances from 1.5 to 16 $mm^2$, such as 4 to 9 $mm^2$.

The cathode and/or the anode may be a large surface area electrode, e.g., as described above. As such, the IEM may include both a large surface area anode and a large surface area cathode. Alternatively, the IEM may include a large surface area anode and a cathode that is commensurate in surface area with the surface area of the side of the circuitry component with which it is associated. In yet other instances, the IEM may include a large surface area cathode and an anode that is commensurate in surface area with the surface area of the side of the circuitry component with which it is associated.

Where the IEM includes a signal amplifier, a large surface area electrode (such as the anode and/or cathode) may extend over at least a portion of the surface of the signal amplifier. In such instances, the portion of the signal amplifier surface which is covered by the large surface area electrode (which may be the anode and/or the cathode) may vary, and in some instances ranges from 50 to 100%, such as 75 to 100%. In these IEMs, the large surface area electrode may be viewed as being at least partially supported by the signal amplifier, i.e., the signal amplifier provides at least a portion of the mechanical support for the electrode.

Figure 8:
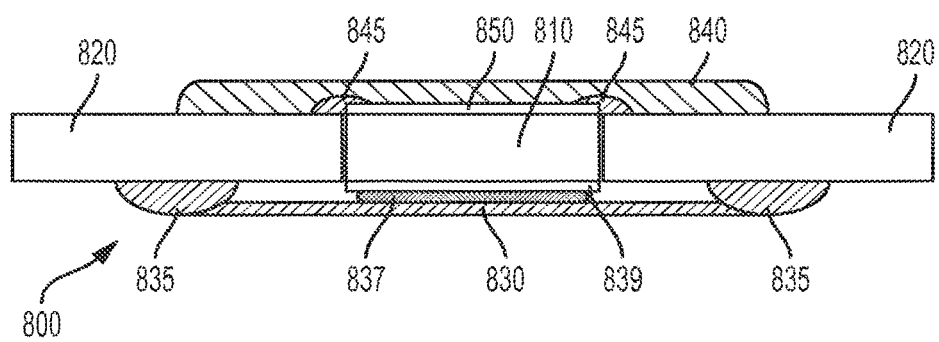
FIG. 8 provides a view of an IEM that includes a large surface area anode and cathode, according to one aspect.

FIG. 8 provides a view of an IEM that includes a large surface area anode and a large surface area cathode according to one aspect. In FIG. 8, device 800 includes controller 810 (labeled "IC" and including circuitry component) encircled by signal amplifier 820 (labeled "skirt"). On the bottom side of controller 810 is a large surface area anode 830, made up of magnesium. Large surface area anode 830 extends over a portion of the signal amplifier, e.g., as described above, and is stably associated with the remaining components of the IEM by adhesive 835, which in the depicted IEM is a UV curable glue. The large surface area anode 830 is electrically coupled to the controller 810 by a layer of carbon ink 837 and another layer of magnesium 839 on the surface of the controller 810. The layer of magnesium 839 has a surface area that is commensurate in size with the surface area of the controller 810, and may have been produced via a vapor deposition protocol, e.g., as summarized above.

Also shown in FIG. 8 is large surface area cathode 840 stably associated with the upper surface of the controller 810. Large surface area cathode 840 extends over a portion of the signal amplifier, e.g., as described above, and is stably associated with the remaining components of the IEM by adhesive 845, which in the depicted IEM is a UV curable glue. The large surface area cathode 840 is electrically coupled to the controller 810 by a layer of gold 850. The layer of gold 850 has a surface area that is commensurate in size with the surface area of the controller 810, and may have been produced via a vapor deposition protocol, e.g., as summarized above. With respect to cathode layer, this can be fabricated from any convenient material, including the materials described above. Cathode materials of interest include, but are not limited to, metallic salts, e.g., copper salts, such as copper salts of iodide, chloride, bromide, sulfate, formate, gluconate, $Fe^{3+}$ salts, e.g., (such as iron sulfate, iron gluconate, iron citrate, iron phosphates (include iron orthophosphate and iron pyrophosphate) etc.), silver salts (such as AgCl, etc.); metals, e.g., gold, platinum, titanium, etc.; other conductive materials, e.g., graphite, etc., and the like. In some instances, the cathode is copper-free, meaning that copper is not present in the cathode. Examples of cathode materials in such instances include, but are not limited to: gold, platinum, graphite, iron salts, silver salts, etc. Copper-free cathodes may have a number of advantages as compared to cathodes which include copper, including but not limited to improved acceptance by the body, better storage stability, etc.

Figure 16A:
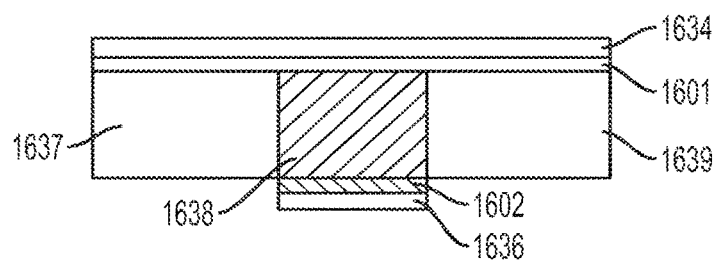
FIGS. 16A-16B are illustrations of one aspect of an event indicator system with increased area for a cathode and/or anode.
Figure 16B:
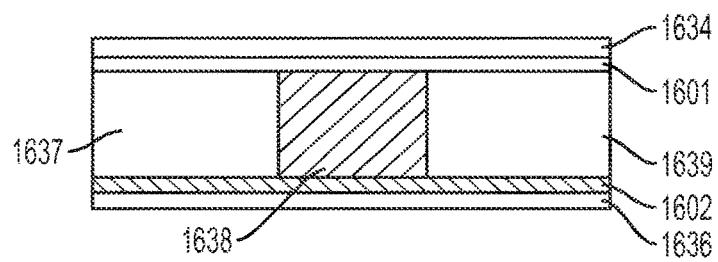

Turning now briefly to FIGS. 16A-16B, FIGS. 16A-16B are illustrations of an aspect of an event indicator system with increased area for a cathode and/or anode. Performance of event indicator system is enhanced when an amplitude of a signal (e.g., which may be used for communications with a receiver) is increased. The signal may be based on current flow derived from ionic exchange as in FIG. 2. Amplitude can be increased by area of the cathode and/or anode used for ionic exchange. Increased amplitude could also be achieved by increasing the size of the control device 38 (e.g., by increasing the size of an integrated circuit of the control device 38), but that approach may not be feasible from a regulatory point of view. Therefore, increasing the size of the cathode, anode, or both advantageously improves system performance without encountering regulatory difficulties.

In one example configuration shown in FIG. 16A, the area of the cathode 1634 (e.g., AgCl) is increased by using a cathode that is formed over a larger area (footprint) than just the area of integrated circuit (IC) controller 1638, which may be part of control device 1638. Thus, cathode 1634 extends over skirt (non-conductive membrane) portions 1637 and 1635 as shown in FIG. 16A. This configuration, in which the cathode extends over a greater extent than the area associated with the IC controller 1638, may be referred to as an off-chip cathode configuration. The anode formed by material 1636 (which is dissimilar to material 1634, and which may be Mg as one example) is confined to the region associated of IC controller 1638 in this example, such that the area of the anode is not increased. In other words, anode 1636 is disposed below IC controller 1638 but is not disposed below skirt portions 1637 or 1635, such that the anode does not extend under the skirt.

The configuration of FIG. 16B may be referred to as an off-chip cathode and anode configuration and is similar to FIG. 16A except that the anode, too, is increased in area, with portions that are disposed under skirt portions 1637 and 1635, respectively. In FIGS. 16A and 16B, a conductive metallic layer such as gold may be disposed below cathode material 1634, and a conductive layer 1602 such as carbon ink may be disposed above anode material 1636.

A configuration in which both the cathode and anode are confined to regions directly above or below the IC (or equivalently, in which neither the cathode nor anode includes a portion above or below a skirt portion) may be referred to as a baseline configuration. Relative to the baseline configuration, the off-chip cathode configuration of FIG. 16A provides increased cathode area and increased amplitude (e.g., of a signal used for communication with a receiver) and current (e.g., based on ionic exchange). In some aspects with the off-chip cathode configuration, amplitude is increased (relative to the baseline configuration) by a factor of about 1.4 and current is also increased (relative to the baseline configuration) by a factor of about 1.4. In some instances with the off-chip cathode and anode configuration, amplitude is increased (relative to the baseline configuration) by a factor of about 2.4, and current is increased (relative to the baseline configuration) by a factor of about two to three. Thus, increasing the area of the cathode or anode individually increases amplitude and current, and increasing the area of both the cathode and the anode further increases amplitude and current. Various processes, described below, may be used to manufacture event marker systems having a cathode and/or anode with increased area relative to the baseline configuration.

Figure 9A:
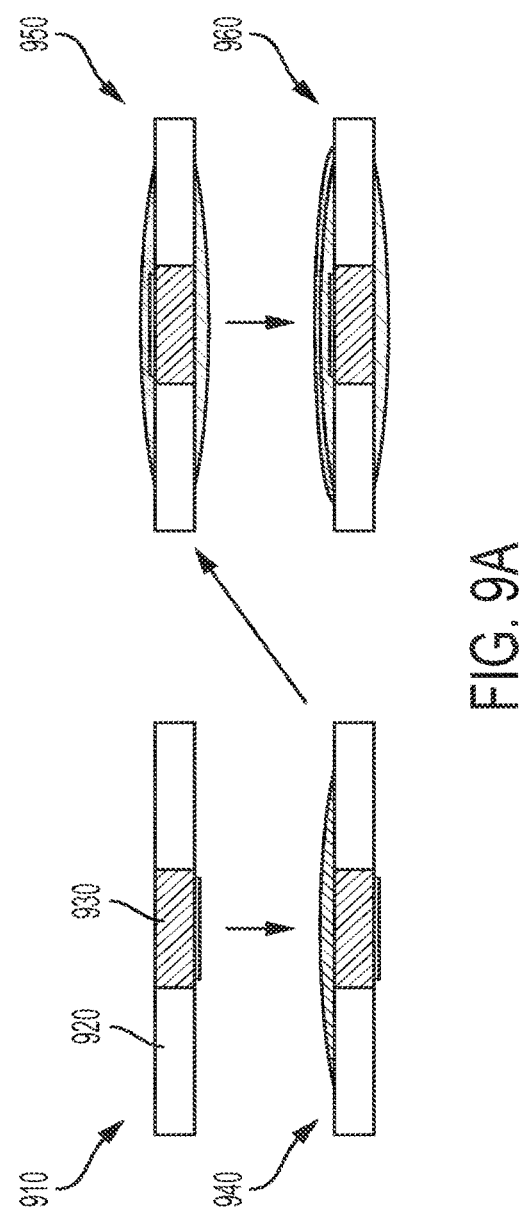
FIG. 9A provides a depiction of print-based fabrication protocol, according to one aspect.

IEMs that include at least one large surface area electrode, e.g., as described above, may be fabricated using any convenient protocol. One type of fabrication protocol of interest is what is referred to herein as "printing" based protocol, in which at least one component of the IEM is produced by depositing a liquid precursor of that component (e.g., which may be referred to herein as an "ink") and then allowing the precursor to solidify to the produce the desired component. An example of a printing based protocol is illustrated in FIG. 9A. As shown, the starting IEM component is produced by placing a controller 930 (circuitry element) into a prefabricated signal amplifier 920 to produce the structure 910. Structure 910 includes a metallic layer, e.g., gold, positioned on one side of the controller. Following this step, liquid anode precursor material 940, e.g., a liquid composition of magnesium (e.g., magnesium metal in a suitable binder and solvent), is deposited on one side of structure 910 and allowed to harden to produce a large surface anode, as shown. Next, a large surface cathode is produced by applying a liquid precursor of the cathode 950 (e.g., CuCl in a suitable binder and solvent, wherein additives may be present, such as carbon, alginate, etc.), to the surface of the structure 910 opposite the anode that was produced in the previous step. The deposited liquid is then allowed to harden, e.g., via solvent evaporation, to produce the desired large surface area cathode on the structure 910. In a final step, optional protective layer 960 is produced over the surface of large surface area cathode 950. Any convenient protective layer composition and structure may be employed. Examples of suitable protective layers include, but are not limited to: protective barrier shelf-life stability components, e.g., as described in U.S. application Ser. No. 13/304,260 filed on Nov. 23, 2011 (the disclosure of which is herein incorporated by reference) and highly-swellable polymeric films, e.g., as described in U.S. Provisional Application Ser. No. 61/758,030 filed on Jan. 29, 2013, the disclosure of which is herein incorporated by reference.

FIG. 9A illustrates another aspect of an event indicator system with an off-chip cathode and anode configuration. FIG. 9A shows a process for making an event indicator system structure 910. A first portion 935 and a second portion 937 of a skirt-type amplifier 920 are disposed on first and second sides, respectively, of the controller 930. A conductive metallic (e.g., gold) layer 901 is disposed at a bottom of the controller 930. An anode material 936 is screen printed or laminated onto the controller 930 such that the anode material 936 extends at least partially over skirt amplifier 920 portions 935 and 937. The anode material 936 may be magnesium, e.g., in the form of an ink, a slurry including a binder and solvent, or a sheet. The apparatus is then flipped (inverted) so that the laminated anode 936 is disposed on the underside of the controller 930 and skirt amplifier 920 portions 935, 937. A cathode material 934 is screen printed or laminated over metallic layer 901 and at least partially over skirt amplifier 920 portions 935, 937. The cathode material 934 may be CuCl, e.g., in the form of an ink or a slurry comprising a binder, carbon, and alginate. A coating 903 may be applied to protect the cathode. The coating 903 may include a polymer film, e.g., a film formed from a polymer matrix such as sodium alginate (which may improve shelf life of the system), sodium carboxymethyl cellulose, or hydroxypropyl cellulose (HPC) (which improves adhesion). The polymer matrix may contain an acidulant (acidulating agent), which is a material that dissolves when in contact with water to generate $H^+$ ions. Examples of acidulating agents include alginic acid, tartaric acid, malic acid, and citric acid, e.g., as described above.

Figure 9B:
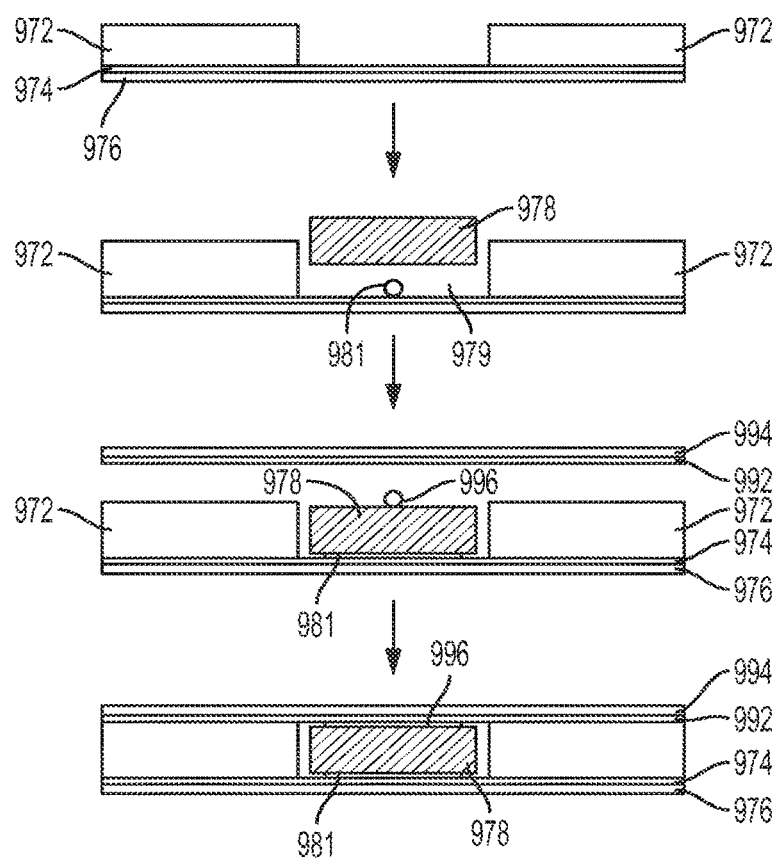
FIG. 9B provides a depiction of a laminate based fabrication protocol, according to one aspect.
Figure 17:
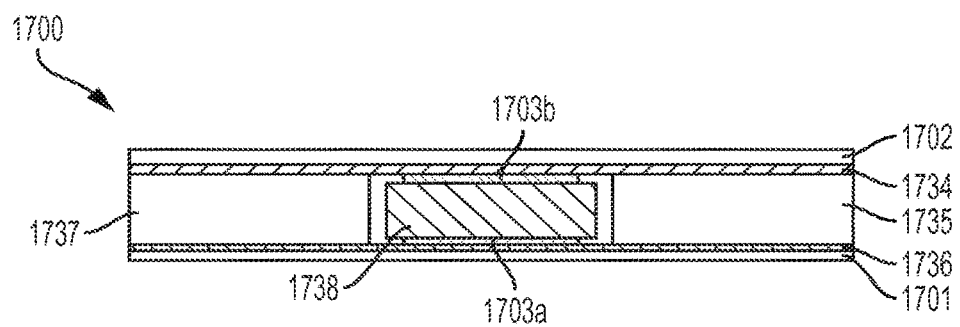
FIG. 17 is an illustration of another aspect of an event indicator system with an off-chip cathode and anode configuration.
Figure 18:
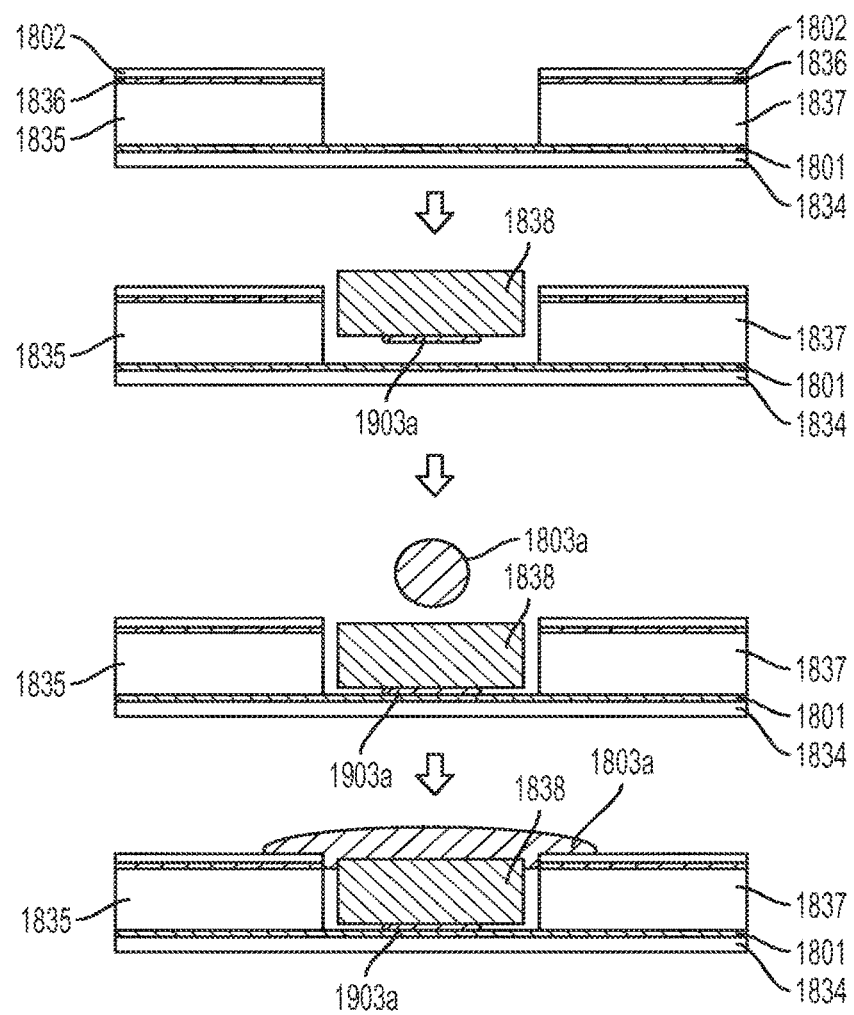
FIG. 18 provides a depiction of fabrication protocol, according to one aspect.

Another type of fabrication protocol of interest is what is referred to herein as a "lamination" based protocol, in which at least one component of the IEM is produced by a lamination process, in which a preformed layer is employed as an IEM component. An example of a printing based protocol is illustrated in FIG. 9B. As shown, a signal amplifier is first applied, either by lamination or print deposition, onto an anode, e.g., magnesium, layer present on a carrier film to produce an initial structure 970. Next, a controller is placed in the cavity of structure 970 to produce the structure 980. The controller may be stably positioned in the cavity and therefore associated with structure 970 using any convenient protocol, such as by using an adhesive, by heat, by mechanical pressure, etc. As shown, an adhesive is positioned at the bottom of the cavity before placement of the controller in the cavity to stably associate the controller in the cavity. Following placement of the controller in the cavity as shown in step 980, a preformed cathode layer sheet on a protective film is positioned on top of the controller and held in place with a conductive adhesive, as shown in step 990, to produce a final IEM as shown. In the product IEM shown, each of the cathode and anode outer surfaces are covered by a protective film, which may or may not be removed prior to use, as desired. Turning now briefly to FIG. 17, FIG. 17 provides an illustration of another aspect of an event indicator system with an off-chip cathode and anode configuration is shown. System 1700 may be made by the following process. A skirt comprising portions 1737 and 1735 is laminated or screen printed onto an anode film comprising anode material 1736 and a carrier film (e.g., polymer film) 1701. IC 1738 is attached to the anode film via heat, conductive adhesive 1703a, or mechanical pressure. A cathode, including cathode material 1734 and protective film 1702, is attached to the skirt portions 1737, 1735 and IC controller 1738 via heat or conductive adhesive 1703b. FIG. 18 is an illustration of a fabrication protocol for preparing the system 1900 illustrated in FIG. 19. In the process shown in FIG. 18, an initial structure 1805 is first provided that includes a skirt amplifier comprising portions 1837 and 1835, where the skirt has attached to a bottom thereof a cathode comprising cathode material 1834 (e.g., CuCl) and metallic (e.g., gold) layer 1801 and has attached to a top thereof an anode comprising anode material 1836 (e.g., Mg) and a carrier film (e.g., polymer film) 1802. These components may be formed by a lamination process, with a hole pre-punched for subsequent placement of an IC. Thus, the anode includes anode portions that are formed over skirt portions 1837 and 1835, respectively. As shown at step 1807, IC controller 1838 has an adhesive 1803a (e.g., carbon ink or ethylcellulose, which may reduce the risk of short-circuiting the IC) applied at a bottom thereof. IC 1838 is attached to the cathode using the adhesive 1803a and is physically separated from cathode material 1836 on either side of the IC 1838. As shown in Step 1809, a conductive layer (e.g., carbon ink) 1850 is printed over the top of the top of IC 1838 to connect to the anode portions that are on either side of IC controller 1838.

Figure 19:
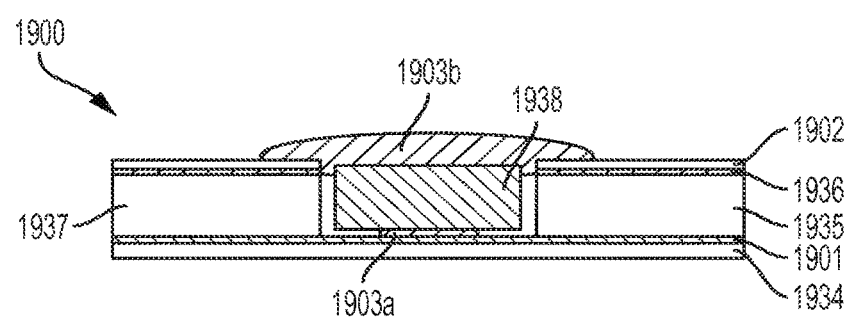
FIG. 19 is an illustration of another aspect of an event indicator system with an off-chip cathode and anode configuration.

FIG. 19 is an illustration of another aspect of an event indicator system with an off-chip cathode and anode configuration, e.g., as made by the protocol shown in FIG. 18. In FIG. 19, a skirt amplifier comprising portions 1937 and 1935 has attached to a bottom thereof a cathode comprising cathode material 1934 (e.g., CuCl) and metallic (e.g., gold) layer 1901 and has attached to a top thereof an anode comprising anode material 1936 (e.g., Mg) and a carrier film (e.g., polymer film) 1902. These components may be formed by a lamination process, with a hole pre-punched for subsequent placement of an IC. Thus, the anode includes anode portions that are formed over skirt portions 1937 and 1935, respectively. IC controller 1938 has an adhesive 1903a (e.g., carbon ink or ethylcellulose, which may reduce the risk of short-circuiting the IC) applied at a bottom thereof. IC 1938 is attached to the cathode using the adhesive 1903a and is physically separated from cathode material 1936 on either side of the IC 1938. A conductive layer (e.g., carbon ink) is printed over the top of the top of IC 1938 to connect to the anode portions that are on either side of IC controller 1938.

Figure 20A:
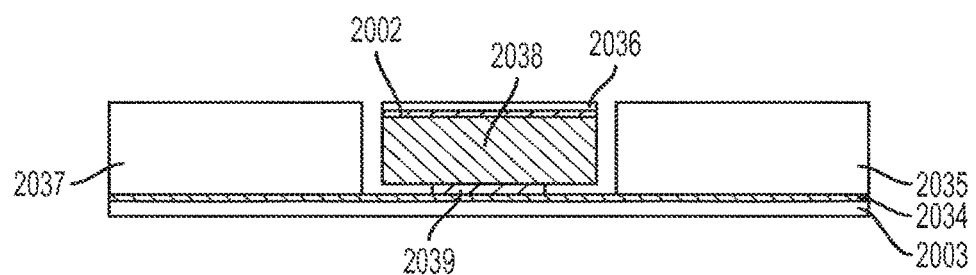
FIGS. 20A-20B are illustrations of aspects of event indicator systems with off-chip cathode and off-chip anode configurations, respectively.
Figure 20B:
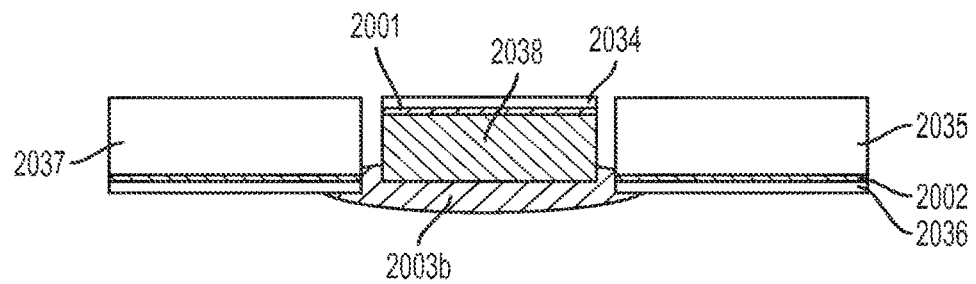

FIGS. 20A-20B are illustrations of aspects of event indicator systems with off-chip cathode and off-chip anode configurations, respectively. FIG. 20A shows an event indicator system 2000a with an off-chip cathode configuration. The cathode is formed as a laminate with cathode material 2034 (e.g., AgCl or CuCl) and a protective film layer 2003. Portions of the cathode (at left and right of FIG. 20A) are disposed under skirt portions 2037 and 2035, respectively, and a central portion of the cathode is disposed below IC controller 2038. The anode is disposed above IC controller 2038 and includes conductive layer 2002 (e.g., carbon ink) and anode material 2036 (e.g., Mg). A conductive adhesive 2003a (e.g., carbon ink) is used to secure the IC to the cathode. Cathode material 2034 is not in direct contact with portions 2037 or 2035 of the skirt.

FIG. 20B shows an event indicator system 2000b with an off-chip anode configuration. The anode is formed as a laminate with anode material 2036 and conductive layer 2002 (e.g., carbon ink), and is disposed under respective skirt portions 2037 and 2035. A conductive metallic (e.g., gold) layer 2001 is formed at the top of IC controller 2038, and cathode material 2034 is formed above layer 2001. Cathode material 2034 is not in direct contact with portions 2037 or 2035 of the skirt. A conductive adhesive 2003b (e.g., carbon ink) electrically couples the IC controller 2038 with the anode portions on either side of the IC controller 2038, although IC controller 2038 is not in direct physical contact with those anode portions.

Figure 21A:
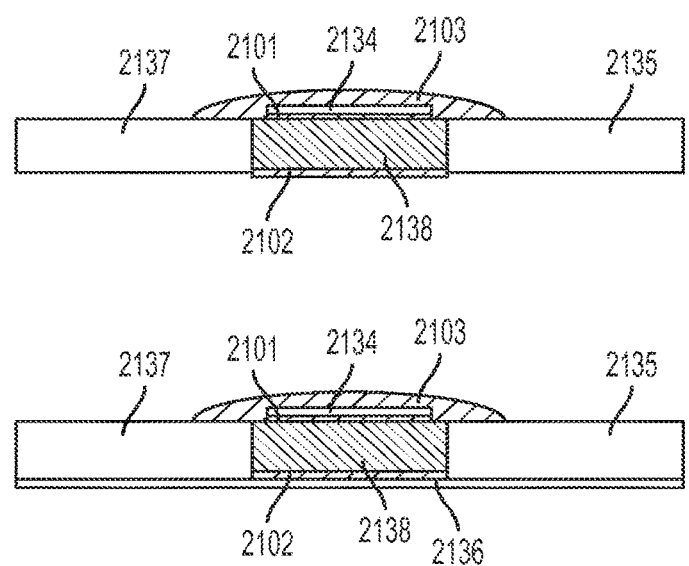
FIGS. 21A-21B are illustrations of an aspect of an event indicator system with an off-chip anode configuration.
Figure 21B:
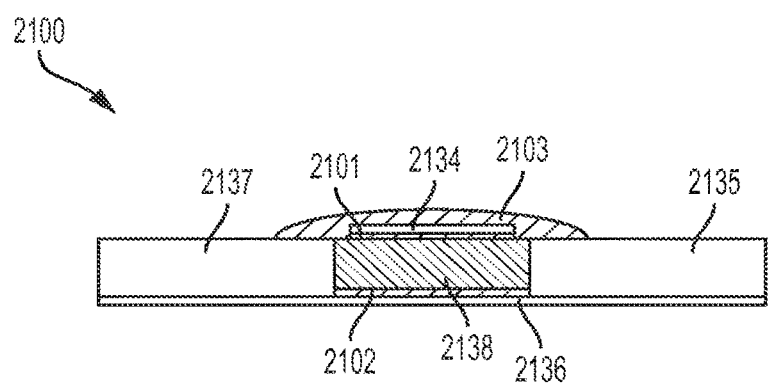

FIGS. 21A and 21B provide illustrations of an aspect of an event indicator system with an off-chip anode configuration and process for preparing the same. As shown at step 2505 of FIG. 21A, an initial structure is provided that includes skirt amplifier portions 2137 and 2135 disposed on either side of IC controller 2138. In the initial structure, a conductive metallic (e.g., gold) layer 2101 and cathode material (e.g., CuCl) are disposed on top of the IC controller 2138. Also in the initial structure, protective film 2103 (e.g., HPC) is formed over the cathode and may extend over amplifier skirt portions 2137 and 2135. A metallic layer (e.g., titanium) 2102 is formed at a bottom of IC controller 2138, e.g., using a deposition process. As shown at step 2106, a layer 2136 of an anode material (e.g., Mg) is formed, e.g., using an evaporation process, with first and second portions below amplifier skirt portions 2137 and 2135, and with a third portion below layer 2102. Anode layer 2136 may have a thickness of about 1 μm in one aspect.

FIG. 21B is an illustration of an aspect of an event indicator system 2100 with an off-chip anode configuration, e.g., as produced using the protocol depicted in FIG. 21A. Skirt amplifier portions 2137 and 2135 are disposed on either side of IC controller 2138. A conductive metallic (e.g., gold) layer 2101 and cathode material (e.g., CuCl) are disposed on top of the IC controller 2138. A protective film 2103 (e.g., HPC) is formed over the cathode and may extend over amplifier skirt portions 2137 and 2135. A metallic layer (e.g., titanium) 2102 is formed at a bottom of IC controller 2138, e.g., using a deposition process. A layer 2136 of an anode material (e.g., Mg) is formed, e.g., using an evaporation process, with first and second portions below amplifier skirt portions 2137 and 2135, and with a third portion below layer 2102. Anode layer 2136 may have a thickness of about 1 μm in one aspect.

In various aspects (e.g., described in relation to FIGS. 16A-21B), the size (area) of the cathode, the anode, or both, is increased by utilizing space above or below a skirt portion for the cathode and/or anode. Thus, the anode, cathode, or both, extends beyond an area associated with the control device that controls conductance between the anode and cathode.

Various materials can be used for the cathode and/or anode, and the current (associated with ionic exchange) and/or amplitude of a signal used for communication with a receiver (discussed further below) are increased mainly due to the geometric characteristic of increased area for the anode and/or cathode, and independent of the specific materials used for the anode and/or cathode. Various sizes for anodes and cathodes have been tested. The size of the cathode does not have to be the same as the size of the anode. For example, a 5 mm skirt has been tested with cathodes of diameters 1 mm, 2 mm, and 3 mm, and with anodes of diameters 1 mm, 2 mm, and 3 mm. In each case, as the diameter of the cathode (or anode) increases, amplitude increases as well, and the increase is greater when the cathode and anode are both increased in size.

In certain aspects, CuCl and/or copper may be eliminated, e.g., by using alternative cathode materials such as AgCl. The elimination of copper is advantageous because systems that do not contain copper are less toxic (and thus better for ingestion), easier to process and store (due to decreased sensitivity to moisture), and provide equivalent or better ingestible event marker performance as systems that contain copper. Increased area of a cathode and/or electrode in certain aspects results in increased battery stability, a more stable frequency (for communications with a receiver, as discussed below), and increased signal-to-noise ratio (SNR). Alternative cathode materials (other than CuCl) may include but are not limited to: iron salts (e.g., ferrous gluconate, ferrous sulfate); gold; copper cupric gluconate; cupric sulfate; tartarate; malate; citrate; iodate; alginate. These alternate cathode materials may not yield equivalent comparable performance as an equivalently sized CuCl cathode, but the increase in cathode (and/or anode) area in certain aspects may compensate for that factor. For example, in certain aspects the cathode and/or anode may be increased in area by a factor between about ten and about fifteen, e.g., a factor of 13 as area is increased from about 0.74 mm2 to about 9.62 mm2. In some aspects, at the anode, a magnesium alloy may be used instead of pure magnesium. For example, additives such as aluminum or zinc may be include in the anode to enhance discharge performance at the anode.

Figure 22:
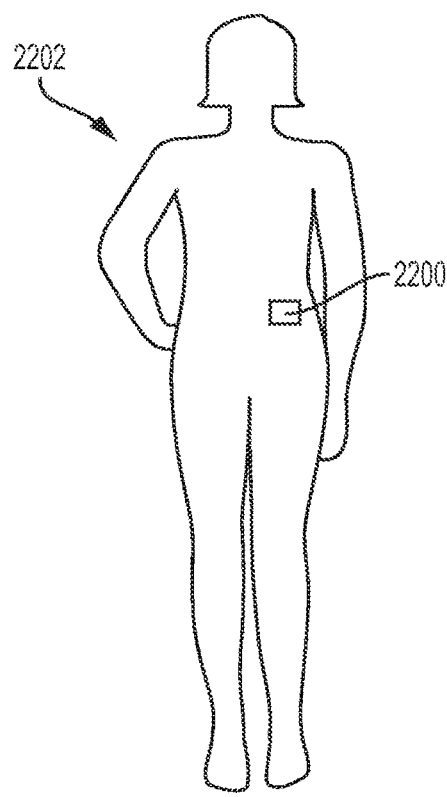
FIG. 22 is a representation of a receiver for detection of data transmission through a living subject.

Referring to FIG. 22, receiver 2200 is shown in position on a living subject 2202. The receiver 2200 is shown attached to a left mid-section of the subject 1302. However, the scope of the present disclosure is not limited by the location of the receiver 2200 on the subject 2202.

IEM Additional Components

Where desired, an IEM may be stably associated in some manner to another ingestible component, e.g., pharmaceutically acceptable carrier component (e.g., as described above). By "stably associated" is meant that the event indicator and second ingestible component, e.g., a pharmaceutically acceptable carrier component, do not separate from each other, at least until administered to the subject in need thereof, e.g., by ingestion.

Pharmaceutically acceptable solid carrier configurations include tablet and capsule configurations. While the pharmaceutically acceptable solid carrier may have a solid configuration, the solid configuration may include a liquid component, such as is found in a liquid capsule, which includes a liquid component present in a solid capsule. In some instances, the pharmaceutically acceptable solid carrier is configured to impart a controlled release profile to an active agent that is associated with the pharmaceutically acceptable solid carrier. Examples of pharmaceutically acceptable solid carriers of interest can be found in Remington's Pharmaceutical Sciences, Mace Publishing Company, Philadelphia, Pa., 17th ed. (1985).

Where desired, the pharmaceutically acceptable solid carrier may include an active agent. Active agents of interest include pharmaceutically active agents as well as non-pharmaceutical active agents, such as diagnostic agents. The phrase "pharmaceutically active agent" (also referred to herein as drugs) refers to a compound or mixture of compounds which produces a physiological result, e.g., a beneficial or useful result, upon contact with a living organism, e.g., a mammal, such as a human. Pharmaceutically active agents are distinguishable from such components as excipients, carriers, diluents, lubricants, binders and other formulating aids, and encapsulating or otherwise protective components. The pharmaceutically active agent may be any molecule, as well as binding portion or fragment thereof, that is capable of modulating a biological process in a living subject. In certain aspects, the pharmaceutically active agent may be a substance used in the diagnosis, treatment, or prevention of a disease or as a component of a medication. The pharmaceutically active agent is capable of interacting with a target in a living subject. The target may be a number of different types of naturally occurring structures, where targets of interest include both intracellular and extracellular targets. Such targets may be proteins, phospholipids, nucleic acids and the like, where proteins are of particular interest. Specific proteinaceous targets of interest include, without limitation, enzymes, e.g., kinases, phosphatases, reductases, cyclooxygenases, proteases and the like, targets comprising domains involved in protein-protein interactions, such as the SH2, SH3, PTB and PDZ domains, structural proteins, e.g., actin, tubulin, etc., membrane receptors, immunoglobulins, e.g., IgE, cell adhesion receptors, such as integrins, etc., ion channels, transmembrane pumps, transcription factors, signaling proteins, and the like. Broad categories of active agents of interest include, but are not limited to: cardiovascular agents; pain-relief agents, e.g., analgesics, anesthetics, anti-inflammatory agents, etc.; nerve-acting agents; chemotherapeutic (e.g., anti-neoplastic) agents; neurological agents, e.g., anti-convulsants, etc. The amount of active agent that is present in the solid carrier may vary. In some instances, the amount of active agent that is present may range from 0.01 to 100% by weight.

Further examples of pharmaceutically acceptable solid carriers and active agents which may or may not be included therein are described in PCT Application Serial No. PCT/US2006/016370 published as WO/2006/116718; PCT Application Serial No. PCT/US2007/082563 published as WO/2008/052136; PCT Application Serial No. PCT/US2007/024225 published as WO/2008/063626; PCT Application Serial No. PCT/US2007/022257 published as WO/2008/066617; PCT Application Serial No. PCT/US2008/052845 published as WO/2008/095183; PCT Application Serial No. PCT/US2008/053999 published as WO/2008/101107; PCT Application Serial No. PCT/US2008/056296 published as WO/2008/112577; PCT Application Serial No. PCT/US2008/056299 published as WO/2008/112578; PCT Application Serial No. PCT/US2008/077753 published as WO2009/042812; PCT Application Serial No. PCT/US2008/085048 published as WO2009/070773; PCT Application Serial No. PCT/US2009/36231 published as WO2009/111664; PCT Application Serial No. PCT/US2009/049618 published as WO2010/005877; PCT Application Serial No. PCT/US2009/053721 published as WO2010/019778; PCT Application Serial No. PCT/US2009/060713 published as WO2010/045385; PCT Application Serial No. PCT/US2009/064472 published as WO2010/057049; PCT Application Serial No. PCT/US2009/067584 published as WO2010/068818; PCT Application Serial No. PCT/US2009/068128 published as WO2010/075115; PCT Application Serial No. PCT/US2010/020142 published as WO2010/080765; PCT Application Serial No. PCT/US2010/020140 published as WO2010/080764; PCT Application Serial No. PCT/US2010/020269 published as WO2010/080843; PCT Application Serial No. PCT/US2010/028518 published as WO2010/111403; PCT Application Serial No. PCT/US2010/032590 published as WO2010/129288; PCT Application Serial No. PCT/US2010/034186 published as WO2010/132331; PCT Application Serial No. PCT/US2010/055522 published as WO2011/057024; the disclosures of which are herein incorporated by reference.

Systems

Also provided are systems that include an ingestible device, e.g., an IEM, and a detection component, e.g., in the form of a receiver. Receivers of interest are those configured to detect, e.g., receive, a communication from an IEM. The signal detection component may vary significantly depending on the nature of the communication that is generated by the ingestible device. As such, the receiver may be configured to receive a variety of different types of signals, including but not limited to: RF signals, magnetic signals, conductive (near field) signals, acoustic signals, etc. In certain aspects, the receiver is configured to receive a signal conductively from an IEM, such that the two components use the body of the patient as a communication medium. As such, communication that is transferred between event indicator and the receiver travels through the body, and requires the body as the conduction medium. The IEM communication may be transmitted through and received from the skin and other body tissues of the subject body in the form of electrical alternating current (a.c.) voltage signals that are conducted through the body tissues. This communication protocol has the advantage that the receivers may be adaptably arranged at any desired location on the body of the subject, whereby the receivers are automatically connected to the required electrical conductor for achieving the signal transmission, i.e., the signal transmission is carried out through the electrical conductor provided by the skin and other body tissues of the subject.

The receivers of interest include external, semi-implantable, and implantable receivers. In external aspects, the receiver is ex vivo, by which is meant that the receiver is present outside of the body during use. Examples include wearable patches, e.g., adhesive patches, torso bands, wrist(s) or arm bands, jewelry, apparel, mobile devices such as phones, attachments to mobile devices, etc. Where the receiver is implanted, the receiver is in vivo. Examples include cardiac can and leads, under-the-skin implants, etc. Semi-implantable devices include those designed to be partially implanted under the skin.

In certain aspects, the receiver may be configured to provide data associated with a received signal to a location external to said subject. For example, the receiver may be configured to provide data to an external data receiver, e.g., which may be in the form of a monitor (such as a bedside monitor), a computer, a personal digital assistant (PDA), phone, messaging device, smart phone, etc. The receiver may be configured to retransmit data of a received communication to the location external to said subject. Alternatively, the receiver may be configured to be interrogated by an external interrogation device to provide data of a received signal to an external location.

Receivers may be configured variously, e.g., with various signal receiving elements, such as electrodes, various integrated circuit components, one or more power components (such as power receivers or batteries), signal transmission components, housing components, etc.

In one aspect, for example, the receiver includes one or more of: a high power-low power module; an intermediary module; a power supply module configured to activate and deactivate one or more power supplies to a high power processing block; a serial peripheral interface bus connecting master and slave blocks; and a multi-purpose connector, as further described in PCT Application Serial No. PCT/US2009/068128 published as WO2010/075115, infra.

Receivers of interest include, but are not limited to, those receivers disclosed in: PCT Application Serial No. PCT/US2006/016370 published as WO 2006/116718; PCT Application Serial No. PCT/US2008/52845 published as WO 2008/095183; PCT Application Serial No. PCT/US2007/024225 published as WO 2008/063626; PCT Application Serial No. PCT/US2008/085048 published as WO 009/070773; PCT Application Serial No. PCT/US2009/068128 published as WO2010/075115; and PCT Application Serial No. US2012/047076 filed on Jul. 21, 2012; the disclosures of which applications (and particularly receiver components thereof) are herein incorporated by reference.

In certain embodiments, the signal receiver includes a set of two or more, such as two or three, electrodes that provide for dual functions of signal receiving and sensing. For example, in addition to receiving signal, the electrodes can also serve additional sensing functions. In certain embodiments, the electrodes are used to generate electrocardiogram data. From that data, there are many kinds of processing that can be done, e.g., to detect various cardiac events, such as tachycardia, fibrillations, heart rate, etc. The obtained electrocardiogram data can be used to titrate medications, or be used for alerts when an important change or significant abnormality in the heart rate or rhythm is detected. This data is also helpful in certain embodiments for monitoring heart rate in patients who do not have pacemakers or as an alternative to patients who might normally require a Holter monitor or a Cardiac Event Monitor, portable devices for continuously monitoring the electrical activity of the heart for twenty-four hours or other devices. An extended recording period is useful for observing occasional cardiac arrthymias that are difficult to identify in shorter time periods.

Figure 10:
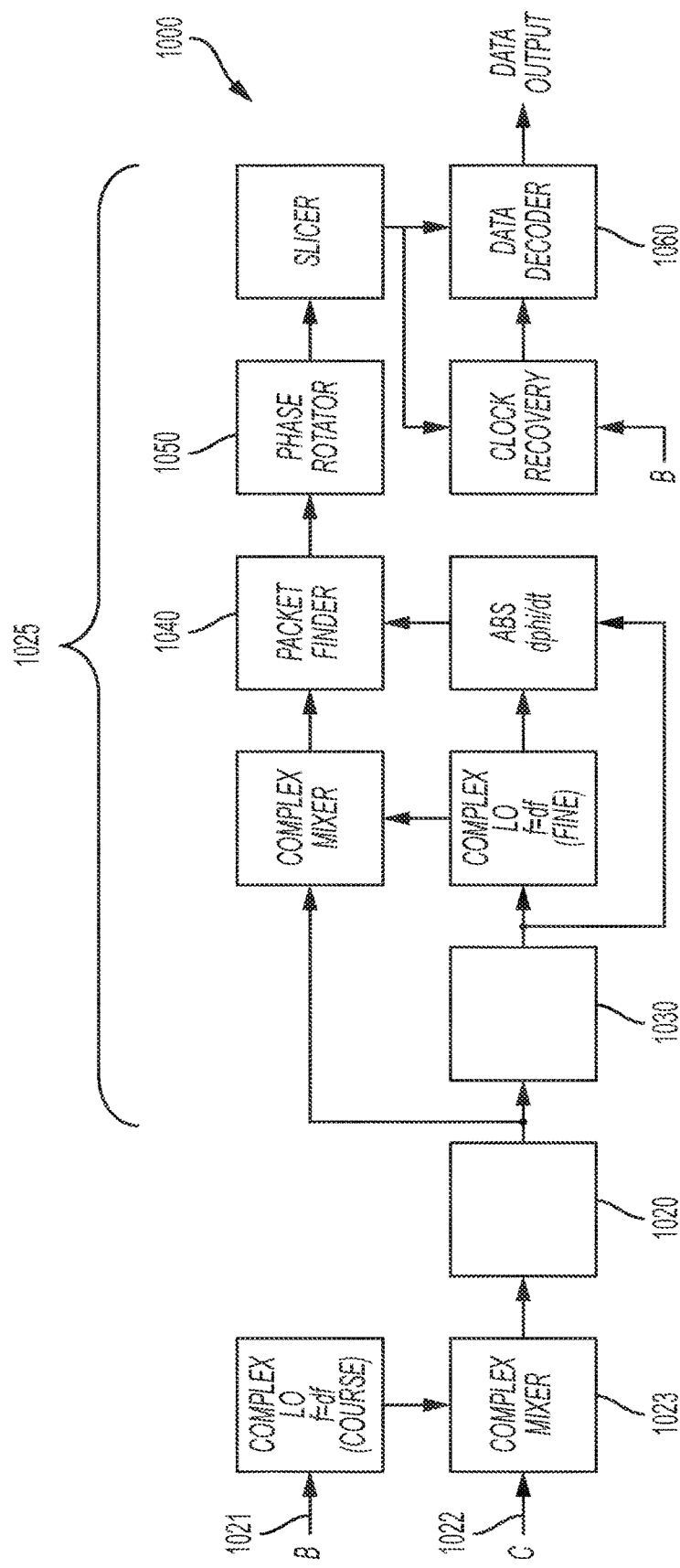
FIG. 10 is a functional block diagram of a demodulation circuit that performs coherent demodulation that may be present in a receiver, according to one aspect.

In some instances, two or more different demodulation protocols may be employed to decode a given received signal. In some instances, both a coherent demodulation protocol and a differential coherent demodulation protocol may be employed. FIG. 10 provides a functional block diagram of how a receiver may implement a coherent demodulation protocol, according to one aspect of the invention. It should be noted that only a portion of the receiver is shown in FIG. 10. FIG. 10 illustrates the process of mixing the signal down to baseband once the carrier frequency (and carrier signal mixed down to carrier offset) is determined. A carrier signal 1021 is mixed with a second carrier signal 1022 at mixer 1023. A narrow low-pass filter 1020 is applied of appropriate bandwidth to reduce the effect of out-of-bound noise. Demodulation occurs at functional blocks 1025 in accordance with the coherent demodulation scheme of the present invention. The unwrapped phase 1030 of the complex signal is determined. An optional third mixer stage, in which the phase evolution is used to estimate the frequency differential between the calculated and real carrier frequency can be applied. The structure of the packet is then leveraged to determine the beginning of the coding region of the BPSK signal at block 1040. Mainly, the presence of the sync header, which appears as an FM porch in the amplitude signal of the complex demodulated signal is used to determine the starting bounds of the packet. Once the starting point of the packet is determined the signal is rotated at block 1050 on the IQ plane and standard bit identification and eventually decoded at block 1060.

In addition to demodulation, the trans-body communication module may include a forward error correction module, which module provides additional gain to combat interference from other unwanted signals and noise. Forward error correction functional modules of interest include those described in PCT Application Serial No. PCT/US2007/024225 published as WO 2008/063626; the disclosure of which application is herein incorporated by reference. In some instances, the forward error correction module may employ any convenient protocol, such as Reed-Solomon, Golay, Hamming, BCH, and Turbo protocols to identify and correct (within bounds) decoding errors.

Receivers of the invention may further employ a beacon functionality module. In various aspects, a beacon switching module may employ one or more of the following: a beacon wakeup module, a beacon signal module, a wave/frequency module, a multiple frequency module, and a modulated signal module.

Figure 11:
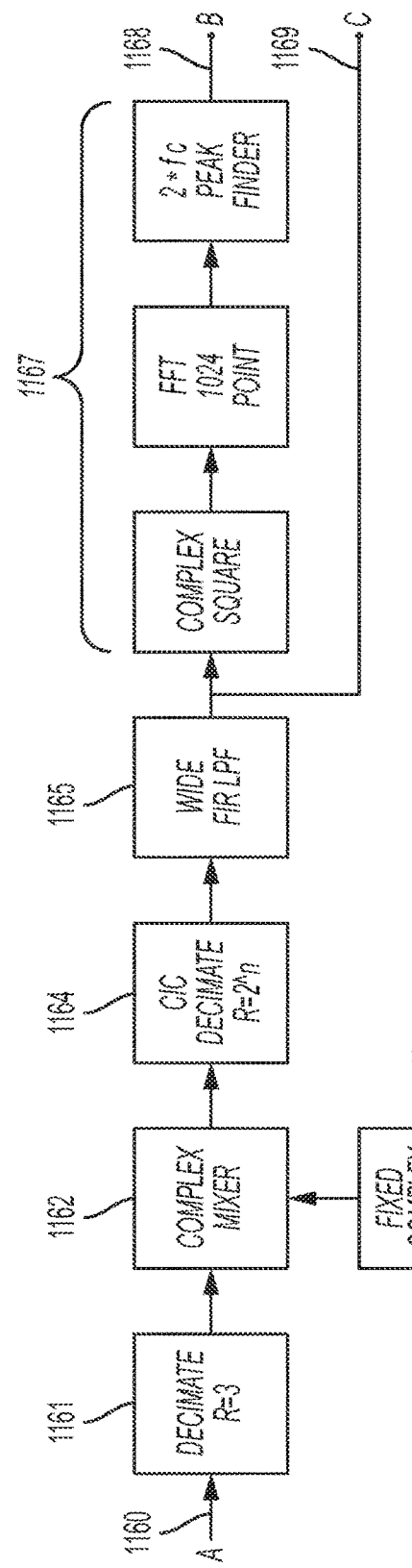
FIG. 11 illustrates a functional block diagram for a beacon module within a receiver, according to one aspect.

A view of a beacon module is provided in the functional block diagram shown in 11. The scheme outlined in FIG. 11 outlines one technique for identifying a valid beacon. The incoming signal 1160 represents the signals received by electrodes, bandpass filtered (such as from 10 KHz to 34 KHz) by a high frequency signaling chain (which encompasses the carrier frequency), and converted from analog to digital. The signal 1160 is then decimated at block 1161 and mixed at the nominal drive frequency (such as, 12.5 KHz, 20 KHz, etc.) at mixer 1162. The resulting signal is decimated at block 1164 and low-pass filtered (such as 5 KHz BW) at block 1165 to produce the carrier signal mixed down to carrier offset-signal 1169. Signal 1169 is further processed by blocks 1167 (fast Fourier transform and then detection of two strongest peaks) to provide the true carrier frequency signal 1168. This protocol allows for accurate determination of the carrier frequency of the transmitted beacon. Further examples of beacon functionality modules are described in PCT Application Serial No. PCT/US2008/085048 published as WO 2009/070773; the disclosure of which application is herein incorporated by reference.

Figure 12:
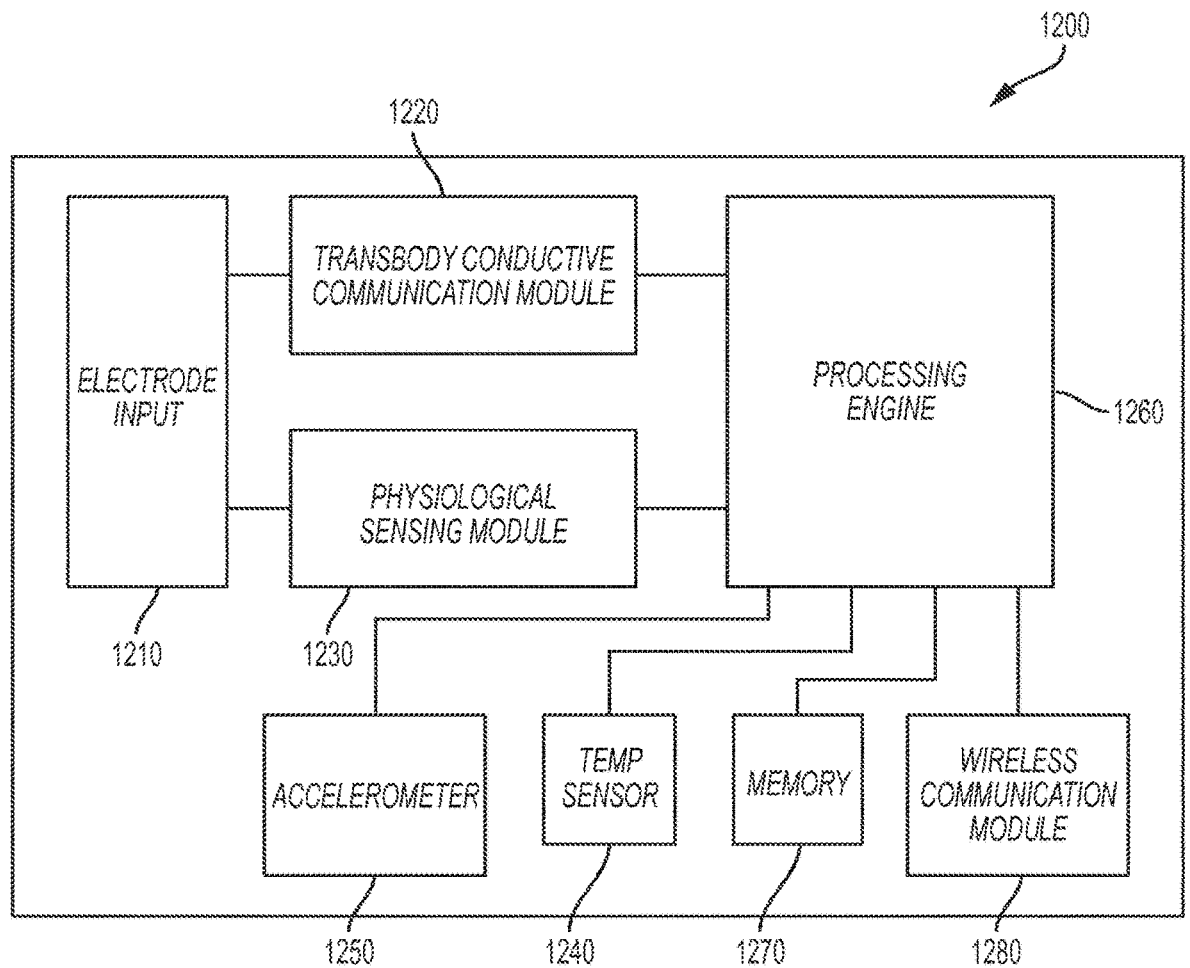
FIG. 12 is a block diagram of different functional modules that may be present in a receiver, according to one aspect.

FIG. 12 provides a block functional diagram of an integrated circuit component of a signal receiver according to an aspect of the invention. In FIG. 12, receiver 1200 includes electrode input 1210. Electrically coupled to the electrode input 1210 are trans-body conductive communication module 1220 and physiological sensing module 1230. In one aspect, trans-body conductive communication module 1220 is implemented as a high frequency (HF) signal chain and physiological sensing module 1230 is implemented as a low frequency (LF) signal chain. Also shown are CMOS temperature sensing module 1240 (for detecting ambient temperature) and a three-axis accelerometer 1250. Receiver 1200 also includes a processing engine 1260 (for example, a microcontroller and digital signal processor), non-volatile memory 1270 (for data storage) and wireless communication module 1280 (for data transmission to another device, for example in a data upload action).

Figure 13:
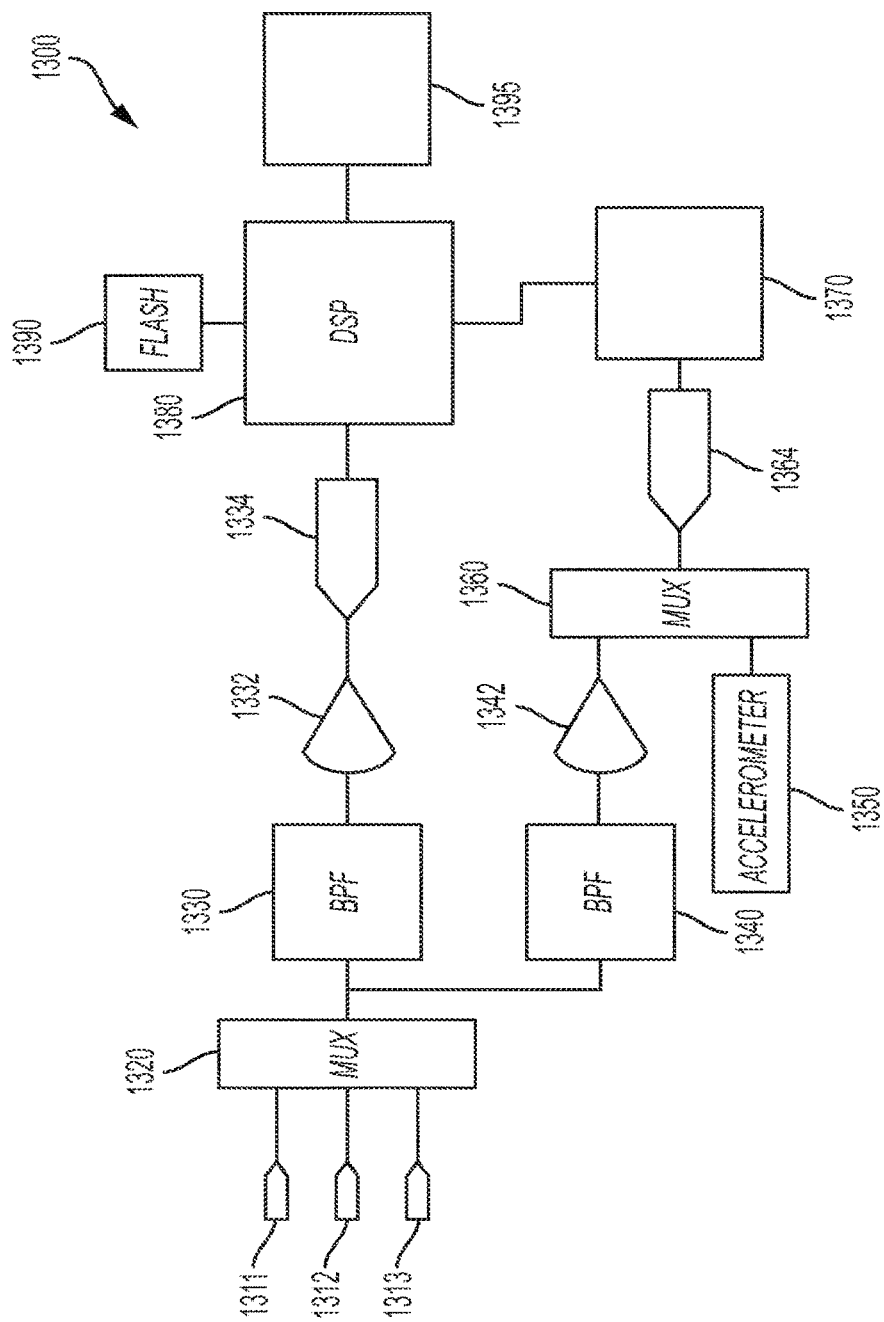
FIG. 13 is a block diagram of a receiver, according to one aspect.

FIG. 13 provides a more detailed block diagram of a circuit configured to implement the block functional diagram of the receiver depicted in FIG. 12, according to one aspect of the invention. In FIG. 13, receiver 1300 includes electrodes e1, e2 and e3 (1311, 1312 and 1313) which, for example, receive the conductively transmitted signals by an IEM and/or sense physiological parameters or biomarkers of interest. The signals received by the electrodes 1311, 1312, and 1313 are multiplexed by multiplexer 1320 which is electrically coupled to the electrodes.

Multiplexer 1320 is electrically coupled to both high band pass filter 1330 and low band pass filter 1340. The high and low frequency signal chains provide for programmable gain to cover the desired level or range. In this specific aspect, high band pass filter 1330 passes frequencies in the 10 KHz to 34 KHz band while filtering out noise from out-of-band frequencies. This high frequency band may vary, and may include, for example, a range of 3 KHz to 300 KHz. The passing frequencies are then amplified by amplifier 1332 before being converted into a digital signal by converter 834 for input into high power processor 1380 (shown as a DSP) which is electrically coupled to the high frequency signal chain.

Low band pass filter 1340 is shown passing lower frequencies in the range of 0.5 Hz to 150 Hz while filtering out out-of-band frequencies. The frequency band may vary, and may include, for example, frequencies less than 300 Hz, such as less than 200 Hz, including less than 150 Hz. The passing frequency signals are amplified by amplifier 1342. Also shown is accelerometer 1350 electrically coupled to second multiplexer 1360. Multiplexer 1360 multiplexes the signals from the accelerometer with the amplified signals from amplifier 1342. The multiplexed signals are then converted to digital signals by converter 1364 which is also electrically coupled to low power processor 1370.

In one aspect, a digital accelerometer (such as one manufactured by Analog Devices), may be implemented in place of accelerometer 1350. Various advantages may be achieved by using a digital accelerometer. For example, because the signals the digital accelerometer would produce signals already in digital format, the digital accelerometer could bypass converter 1364 and electrically couple to the low power microcontroller 1370—in which case multiplexer 1360 would no longer be required. Also, the digital signal may be configured to turn itself on when detecting motion, further conserving power. In addition, continuous step counting may be implemented. The digital accelerometer may include a FIFO buffer to help control the flow of data sent to the low power processor 1370. For instance, data may be buffered in the FIFO until full, at which time the processor may be triggered to turn awaken from an idle state and receive the data.

Low power processor 1370 may be, for example, an MSP430 microcontroller from Texas Instruments. Low power processor 1370 of receiver 800 maintains the idle state, which as stated earlier, requires minimal current draw—e.g., 10 μA or less, or 1 μA or less.

High power processor 1380 may be, for example, a VC5509 digital signal process from Texas Instruments. The high power processor 1380 performs the signal processing actions during the active state. These actions, as stated earlier, require larger amounts of current than the idle state—e.g., currents of 30 μA or more, such as 50 μA or more—and may include, for example, actions such as scanning for conductively transmitted signals, processing conductively transmitted signals when received, obtaining and/or processing physiological data, etc.

The receiver may include a hardware accelerator module to process data signals. The hardware accelerator module may be implemented instead of, for example, a DSP. Being a more specialized computation unit, it performs aspects of the signal processing algorithm with fewer transistors (less cost and power) compared to the more general purpose DSP. The blocks of hardware may be used to "accelerate" the performance of important specific function(s). Some architectures for hardware accelerators may be "programmable" via microcode or VLIW assembly. In the course of use, their functions may be accessed by calls to function libraries.

The hardware accelerator (HWA) module comprises an HWA input block to receive an input signal that is to be processed and instructions for processing the input signal; and, an HWA processing block to process the input signal according to the received instructions and to generate a resulting output signal. The resulting output signal may be transmitted as needed by an HWA output block.

Figure 14:
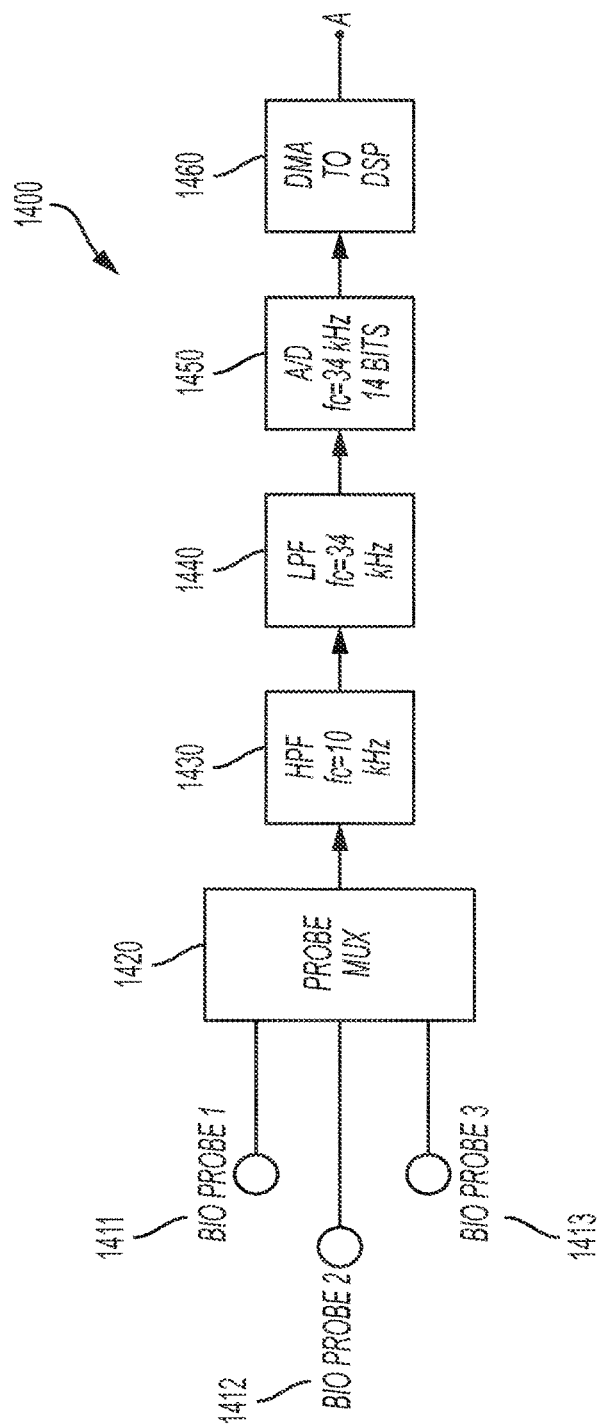
FIG. 14 provides a block diagram of a high frequency signal chain in a receiver, according to one aspect.

FIG. 14 provides a view of a block diagram of hardware in a receiver according to an aspect of the invention related to the high frequency signal chain. In FIG. 14, receiver 1400 includes receiver probes (for example in the form of electrodes 1411, 1412 and 1413) electrically coupled to multiplexer 1420. Also shown are high pass filter 1430 and low pass filter 1440 to provide for a band pass filter which eliminates any out-of-band frequencies. In the aspect shown, a band pass of 10 KHz to 34 KHz is provided to pass carrier signals falling within the frequency band. Example carrier frequencies may include, but are not limited to, 12.5 KHz and 20 KHz. One or more carriers may be present. In addition, receiver 1400 includes analog to digital converter 1450—for example, sampling at 500 KHz. The digital signal can thereafter be processed by the DSP. Shown in this aspect is DMA to DSP unit 1460 which sends the digital signal to dedicated memory for the DSP. The direct memory access provides the benefit of allowing the rest of the DSP to remain in a low power mode.

Figure 15:
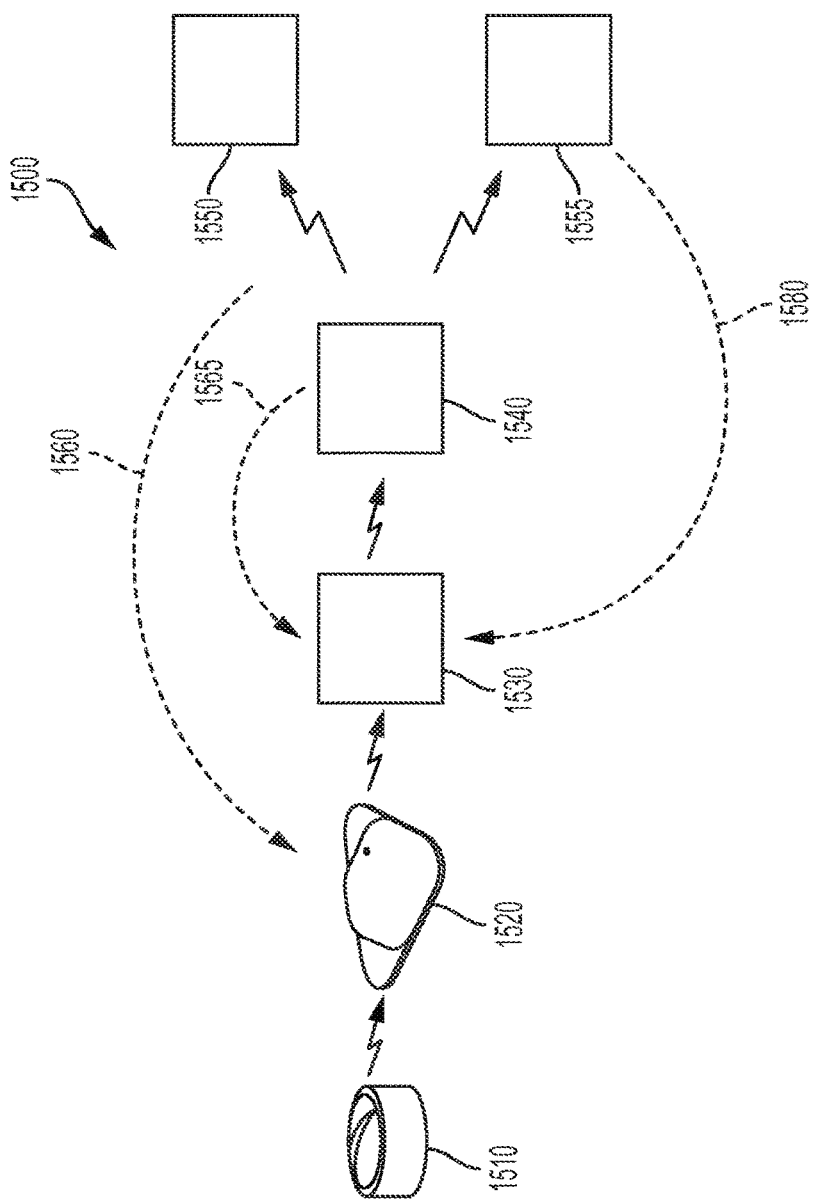
FIG. 15 provides a diagram of how a system that includes a signal receiver and an ingestible event marker may be employed, according to one aspect.

An example of a system of the invention is shown in FIG. 15. In FIG. 15, system 1500 includes a pharmaceutical composition 1510 that comprises an IEM. Also present in system 1500 is signal receiver 1520, such as the signal receiver illustrated in FIGS. 10 to 12. Signal receiver 1520 is configured to detect a signal emitted from the identifier of the IEM 1510. Signal receiver 1520 also includes physiologic sensing capability, such as ECG and movement sensing capability. Signal receiver 1520 is configured to transmit data to a patient's an external device or PDA 1530 (such as a smart phone or other wireless communication enabled device), which in turn transmits the data to a server 1540. Server 1540 may be configured as desired, e.g., to provide for patient directed permissions. For example, server 1540 may be configured to allow a family caregiver 1550 to participate in the patient's therapeutic regimen, e.g., via an interface (such as a web interface) that allows the family caregiver 1550 to monitor alerts and trends generated by the server 1540, and provide support back to the patient, as indicated by arrow 1560. The server 1540 may also be configured to provide responses directly to the patient, e.g., in the form of patient alerts, patient incentives, etc., as indicated by arrow 1565 which are relayed to the patient via PDA 1530. Server 1540 may also interact with a health care professional (e.g., RN, physician) 1555, which can use data processing algorithms to obtain measures of patient health and compliance, e.g., wellness index summaries, alerts, cross-patient benchmarks, etc., and provide informed clinical communication and support back to the patient, as indicated by arrow 1580.

Systems of the invention may include an external device which is distinct from the receiver (which may be implanted or topically applied in certain aspects), where this external device provides a number of functionalities. Such an apparatus can include the capacity to provide feedback and appropriate clinical regulation to the patient. Such a device can take any of a number of forms. By example, the device can be configured to sit on the bed next to the patient, e.g., a bedside monitor. Other formats include, but are not limited to, PDAs, phones, such as smart phones, computers, etc. The device can read out the information described in more detail in other sections of the subject patent application, both from pharmaceutical ingestion reporting and from physiological sensing devices, such as is produced internally by a pacemaker device or a dedicated implant for detection of the pill.

The purpose of the external apparatus is to get the data out of the patient and into an external device. One feature of the external apparatus is its ability to provide pharmacologic and physiologic information in a form that can be transmitted through a transmission medium, such as a telephone line, to a remote location such as a clinician or to a central monitoring agency.

Methods of Use

Aspects of the invention further include methods of using the compositions, such as those described above. Aspects of such methods include administering an ingestible composition to a subject, e.g., by self-administration or via the assistance of another, such as a health care practitioner. Such methods may include placing the ingestible composition in the mouth of a subject such that the subject swallows the ingestible composition. In this manner, the subject ingests the ingestible composition. Ingestible compositions may be employed with a variety of subjects. Subjects of interest include "mammals" including animals classified in the orders carnivore (e.g., dogs and cats), rodentia (e.g., mice, guinea pigs, and rats), and primates (e.g., humans, chimpanzees, and monkeys). In certain aspects, the subjects will be humans.

Following ingestion, the methods may include receiving a signal emitted from an ingestible composition, such as an IEM comprising ingestible composition, e.g., at a receiver, such as described above. In some instances, the received signal is a conductively transmitted signal.

Ingestible compositions may be employed in a variety of different applications. Applications of interest in which the ingestible composition comprises an IEM include, but are not limited to: monitoring patient compliance with prescribed therapeutic regimens; tailoring therapeutic regimens based on patient compliance; monitoring patient compliance in clinical trials; monitoring usage of controlled substances; monitoring the occurrence of a personal event of interest, such as the onset of symptoms, etc., and the like. Applications of interest are further described in PCT Application Serial No. PCT/US2006/016370 published as WO/2006/116718; PCT Application Serial No. PCT/US2007/082563 published as WO/2008/052136; PCT Application Serial No. PCT/US2007/024225 published as WO/2008/063626; PCT Application Serial No. PCT/US2007/022257 published as WO/2008/066617; PCT Application Serial No. PCT/US2008/052845 published as WO/2008/095183; PCT Application Serial No. PCT/US2008/053999 published as WO/2008/101107; PCT Application Serial No. PCT/US2008/056296 published as WO/2008/112577; PCT Application Serial No. PCT/US2008/056299 published as WO/2008/112578; and PCT Application Serial No. PCT/US2008/077753 published as WO2009/042812; the disclosures of which applications is herein incorporated by reference.

Kits

Also provided are kits that include one or more ingestible compositions, such as described above. In those aspects having a plurality of ingestible compositions, the ingestible compositions may be packaged in a single container, e.g., a single tube, bottle, vial, and the like, or one or more dosage amounts may be individually packaged such that certain kits may have more than one container of ingestible compositions. In certain aspects the kits may also include a receiver, such as reviewed above. In certain aspects, the kits may also include an external monitor device, e.g., as described above, which may provide for communication with a remote location, e.g., a doctor's office, a central facility etc., which obtains and processes data obtained about the usage of the composition.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other aspects, the instructions are present as an electronic storage data file present on a suitable computer readable storage medium, e.g. CD-ROM, diskette, etc. In yet other aspects, the actual instructions are not present in the kit, but means for obtaining the instructions from a remote source, e.g. via the internet, are provided. An example of this aspect is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many aspects of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

It is to be understood that this invention is not limited to particular aspects described, as such may vary. It is also to be understood that the terminology used herein is for the purpose of describing particular aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual aspects described and illustrated herein has discrete components and features which may be readily separated from or combined with the features of any of the other several aspects without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

What is claimed is:

1. An ingestible event marker, comprising:
    a support;
    a circuitry secured to the support;
    a signal amplifier secured to the support and encircling the circuitry;
    a first layer of anode material coupled to the circuitry;
    a second layer of first conductive material coupled to the first layer of anode material;
    a third layer of anode material electrically coupled to the second layer of first conductive material and secured on two opposite ends of the third layer to the signal amplifier by a first and a second adhesive, respectively;
    a fourth layer of second conductive material coupled to the circuitry and positioned on the circuitry opposite to the first layer, second layer and third layer; and
    a fifth layer of cathode material coupled to the fourth layer of second conductive material and the signal amplifier by a third and a fourth adhesive.

2. The ingestible event marker of claim 1, wherein the first layer of anode material has a surface area commensurate in size with a surface area of the circuitry that is exposed on one side facing the third layer of anode material.

3. The ingestible event marker of claim 1, wherein an air gap is present between the third layer of anode material and the signal amplifier in an area between an end of the first layer of anode material and the first adhesive.

4. The ingestible event marker of claim 1, wherein the first conductive material comprises carbon ink.

5. The ingestible event marker of claim 1, wherein the second conductive material comprises gold.

6. The ingestible event marker of claim 1, wherein the first layer of anode material comprises magnesium.

7. The ingestible event marker of claim 1, wherein the first layer of cathode material comprises copper chloride.

8. The ingestible event marker of claim 1, wherein the signal amplifier is non-conductive and is configured to extend a current path of a signal being transmitted by the circuitry through a conductive liquid medium.

9. The ingestible event marker of claim 1, wherein the third layer of anode material extending beyond a surface area of the circuitry is configured to increase an amplitude of a signal transmitted by the circuitry.

10. The ingestible event marker of claim 1, wherein the fifth layer of cathode material extends beyond a surface area of the circuitry and is configured to increase an amplitude of a signal transmitted by the circuitry by a factor of about 1.4, compared to if the fifth layer of cathode material extended only across the surface area of the circuitry.

11. The ingestible event marker of claim 1, wherein the third layer of anode material extends beyond a surface area of the circuitry and the fifth layer of cathode material extends beyond the surface area of the circuitry, and the combination of the third layer of anode material and the fifth layer of cathode material extending beyond the surface area of the circuitry is configured to increase an amplitude of a signal transmitted by the circuitry by a factor of about 2.4, compared to if the third layer of anode material extended only across the surface area of the circuitry and the fifth layer of cathode material extended only across the surface area of the circuitry.

12. The ingestible event marker of claim 1, wherein a gap is disposed between the circuitry and the third layer of anode material such that the circuitry is not in direct contact with the third layer of anode material.

* * * * *